US011337683B2

(12) United States Patent
Zhang et al.

(10) Patent No.: US 11,337,683 B2
(45) Date of Patent: May 24, 2022

(54) DEGRADABLE OCCLUDER

(71) Applicant: MALLOW MEDICAL (SHANGHAI) CO., LTD., Shanghai (CN)

(72) Inventors: Jin Zhang, Shanghai (CN); Jian Zhang, Shanghai (CN); Caixia Ma, Shanghai (CN)

(73) Assignee: MALLOW MEDICAL (SHANGHAI) CO., LTD., Shanghai (CN)

( * ) Notice: Subject to any disclaimer, the term of this patent is extended or adjusted under 35 U.S.C. 154(b) by 475 days.

(21) Appl. No.: 16/066,399

(22) PCT Filed: Apr. 8, 2016

(86) PCT No.: PCT/CN2016/078756
§ 371 (c)(1),
(2) Date: Jun. 27, 2018

(87) PCT Pub. No.: WO2017/113531
PCT Pub. Date: Jul. 6, 2017

(65) Prior Publication Data
US 2019/0076136 A1 Mar. 14, 2019

(30) Foreign Application Priority Data

Dec. 31, 2015 (CN) .......................... 201521137500.6
Dec. 31, 2015 (CN) .......................... 201521137627.8
(Continued)

(51) Int. Cl.
*A61B 17/12* (2006.01)
*A61B 17/00* (2006.01)
*A61F 2/00* (2006.01)

(52) U.S. Cl.
CPC .... *A61B 17/0057* (2013.01); *A61B 17/12122* (2013.01); *A61B 17/12172* (2013.01);
(Continued)

(58) Field of Classification Search
CPC .......... A61B 17/0057; A61B 17/12122; A61B 17/12172; A61B 17/12168;
(Continued)

(56) References Cited

U.S. PATENT DOCUMENTS 6,241,768 B1 * 6/2001 Agarwal ............... A61F 2/0063
606/151
8,480,709 B2 7/2013 Chanduszko et al.
(Continued)

FOREIGN PATENT DOCUMENTS

CN 104001221 A 8/2014
CN 204016366 U 12/2014
(Continued)

OTHER PUBLICATIONS

International Search Report and Written Opinion of PCT/CN2016/078756 dated Sep. 28, 2016.
(Continued)

*Primary Examiner* — Katherine H Schwiker
(74) *Attorney, Agent, or Firm* — Dilworth IP, LLC

(57) ABSTRACT

A degradable occluder, which comprises a first disc-shaped mesh, a tubular mesh, and a second disc-shaped mesh, which are sequentially connected, wherein both ends of the tubular mesh are respectively connected to the first disc-shaped mesh and the second disc-shaped mesh, wherein the first disc-shaped mesh, the tubular mesh, and the second disc-shaped mesh are integrally formed. The second disc-shaped mesh is provided with a connector used for closing the mesh surface wherein the connector is formed by heat-melting the mesh body of the second disc-shaped mesh, wherein the materials of the first disc-shaped mesh, the tubular mesh, the second disc-shaped mesh and the connector are all degradable materials. The closing structure of the occluder by closing line increases the support and resilience of the (Continued)

occluder, wherein it reduces manufacturing difficulty and cost.

20 Claims, 16 Drawing Sheets

(30) Foreign Application Priority Data

Dec. 31, 2015 (CN) .......................... 201521137713.9
Dec. 31, 2015 (CN) .......................... 201521137730.2
Dec. 31, 2015 (CN) .......................... 201521138998.8

(52) U.S. Cl.
CPC ..... *A61B 17/12* (2013.01); *A61B 2017/00004* (2013.01); *A61B 2017/00243* (2013.01); *A61B 2017/00477* (2013.01); *A61B 2017/00526* (2013.01); *A61B 2017/00575* (2013.01); *A61B 2017/00592* (2013.01); *A61B 2017/00606* (2013.01); *A61B 2017/00831* (2013.01); *A61F 2/0063* (2013.01)

(58) Field of Classification Search
CPC .... A61B 17/12177; A61B 2017/00575; A61B 2017/00592; A61B 2017/00606; A61B 2017/00004; A61B 2017/00579–00632; A61F 2/0063; A61F 2002/0068
See application file for complete search history.

(56) References Cited

U.S. PATENT DOCUMENTS

| | | | |
|---|---|---|---|
| 8,945,158 B2 | 2/2015 | Devellian et al. | |
| 2005/0228434 A1 | 10/2005 | Amplatz et al. | |
| 2007/0167980 A1 | 7/2007 | Figulla et al. | |
| 2007/0208376 A1* | 9/2007 | Meng | A61B 17/0057 606/213 |
| 2007/0225760 A1 | 9/2007 | Moszner et al. | |
| 2009/0281567 A1 | 11/2009 | Osypka | |
| 2012/0071918 A1 | 3/2012 | Amin et al. | |
| 2013/0178886 A1* | 7/2013 | Liu | D04C 1/06 606/198 |
| 2014/0194921 A1* | 7/2014 | Akpinar | A61B 17/0057 606/200 |
| 2014/0257360 A1* | 9/2014 | Keillor | A61B 17/12122 606/198 |
| 2017/0135801 A1* | 5/2017 | Delaney, Jr. | A61F 2/01 |

FOREIGN PATENT DOCUMENTS

| | | |
|---|---|---|
| CN | 204181658 | 3/2015 |
| CN | 204181743 U | 3/2015 |
| CN | 205322379 U | 6/2016 |
| CN | 205322380 U | 6/2016 |
| CN | 205322403 U | 6/2016 |
| CN | 205322404 U | 6/2016 |
| CN | 205322407 U | 6/2016 |
| CN | 205433769 U | 8/2016 |
| CN | 205433805 U | 8/2016 |
| CN | 206995284 U | 2/2018 |
| EP | 2617386 A | 7/2013 |
| JP | 2005-261951 A | 9/2005 |
| JP | 2009-529994 A | 8/2009 |
| JP | 2015-501691 A | 1/2015 |
| WO | 2013076276 A | 5/2013 |

OTHER PUBLICATIONS

Decision of Rejection of Priority application CN201521137500.6 dated Nov. 1, 2016.
The First Office Action of Priority Application CN201521137500.6 dated Apr. 22, 2016.
Decision of Reexamination of Priority Application CN 201521137500.6 dated Mar. 6, 2018.
Decision of Rejection of Priority application CN201521137627.8 dated Oct. 28, 2016.
The First Office Action of Priority Application CN201521137627.8 dated Apr. 20, 2016.
Decision of Reexamination of Priority application CN201521137627.8 dated Feb. 13, 2018.
The First Office Action of Priority Application CN201521138998.8 dated Apr. 20, 2016.
Decision of Rejection of Priority Application CN201521138998.8 dated Oct. 28, 2016.
Decision of Reexamination of Priority Application CN201521138998.8 dated Dec. 14, 2017.
Extended European Search Report issued in European patent application No. 16880339.3 dated Apr. 12, 2019.
Notice of Reasons for Refusal issued in Japanese patent application No. 2018-553276 dated May 14, 2019.
First Office Action of Singapore Application 11201805561S dated Oct. 17, 2019.
Second Office Action of Singapore Application 11201805561S dated Nov. 9, 2020.
Partial Supplementary European Search Report issued in European Application No. 16880339.3 dated Jan. 3, 2019.
PCT International Search Report and Written Opinion dated Sep. 28, 2016 from Application No. PCT/CN2016/078756, 13 pages.
Third Office Action of Singapore Application 11201805561S dated Oct. 25, 2021, 12 pages.

* cited by examiner

DEGRADABLE OCCLUDER

This application claims the priority of the Chinese patent applications CN201521137713.9, CN201521137500.6, CN201521137730.2, CN201521138998.8, and CN 201521137627.8 with filing dates of Dec. 31, 2015. This application refers to the full texts of the above-mentioned Chinese patent applications.

FIELD OF INVENTION

The present invention relates to a degradable occluder for use in the interventional treatment of structural heart disease.

BACKGROUND OF THE INVENTION

Atrial septal defect, patent ductus arteriosus, ventricular septal defect, patent foramen ovale, and left atrial appendage are common structural heart diseases. The traditional treatment is surgery. Surgical treatment methods, patients need to open the chest by surgery. Its biggest drawbacks are: (1) surgery requires extracorporeal circulation, so surgery may cause complications and lead to death; (2) surgical trauma is obvious which leaves postoperative scars; (3) surgery is expensive.

Since the 1980s, with the development and improvement of catheter interventional diagnosis and treatment technology, China gradually introduced minimally invasive interventional technology to treat structural heart disease. The method of minimally invasive interventional treatment of structural heart disease has developed rapidly and is now very mature. Compared with traditional surgery, minimally invasive interventional treatment is a modern high-tech minimally invasive treatment. Through the femoral vein puncture and under the guidance of medical imaging equipment, the guide wire is minimally invasively introduced into the femoral vein or the small surgical incision of heart. Subsequently, the delivery catheter was placed at the defect or abnormal site by the guide wire. Finally, the occluder was pushed along the delivery catheter to the defect or abnormal site for closure treatment. Such minimally invasive interventional therapy has the advantages of less trauma, no need for extracorporeal circulation, less complications, quicker recovery, better results, a wider range of indications and relatively lower surgical costs.

The treatment of implanted occluders by minimally invasive interventional surgery has many advantages over traditional surgical procedures. However, since the material used for the main stent of clinically used occluders is mainly nickel-titanium alloy wire and such metal materials cannot be degraded, long-term implantation may cause inflammation, coagulation, and other reactions in human tissues, even cause some extent damage. Therefore there are certain flaws which may still have the following use risks: (1) nitinol is a non-degradable metal alloy material. Although its biocompatibility has been demonstrated, the long-term risk of the permanent implantation still can't get full control; (2) there was less long-term follow-up data about the safety of permanently retaining on the heart to the human body and the effect of the fixed size of the occluder on the child's growing heart. Because the nitinol occluder is permanently implanted and non-degradable, it may affect the development of the heart in immature patients; (3) there are still no clear scientific arguments for complications such as nickel deposition and nickel allergy. (4) patients are hindered from receiving other cardiac interventions in the long term.

After the occluder surface is completely endothelialized and the heart defect is repaired by the body's own tissue, the occluder is not necessary to be retained in the body. Therefore, the ideal occluder should provide a temporary bridge for the repair of the heart itself. It is degraded by the body after the historical mission is completed so that the defect is completely repaired by the self-tissue. Thus it will avoid the long-term complications and hidden dangers caused by metal retention.

The supporting structure of the degradable occluder described in U.S. Pat. No. 8,480,709 B2 is cut from a pipe. The connection points of the two disc surfaces of the occluder are similar to the two welding points of the occluder. The center of the two disc surfaces is convex, which cause the risk of local thrombosis on the surface of the occluder. It is also not conducive to the process of endothelialization of the occluder surface. At the same time, the release length of the occluder is longer during the implantation procedure, which can easily damage the heart tissue. The occluder manufactured by this method has poor compliance and recovery and needs a locking device to help it return to its original shape. The introduction of the locking device will greatly increase the difficulty of the doctor's intraoperative operation. If the occluder selected at the beginning is not suitable, it is more difficult to retract the occluder to the delivery sheath, which will greatly increase the risk of surgery. In some of these designs, once the locking device has been locked into the occluder it is impossible to re-acquire into the delivery sheath for replacement. If the occluder chosen initially is not suitable it can only be retrieved by surgical operation.

In the patent, the mesh surface of the occluder without the connector adopts the structure of closing line to close the end of the occluder to make the outer mesh surface more flat, which can reduce the risk of local thrombus formation and accelerate the process of endothelialization on the surface of the occluder. The process of endothelialization allows the defect to be repaired earlier by its own tissue. At the same time, the release length of the occluder is reduced during the operation, which can greatly reduce the damage to the heart and make the operation more effective and safer. The occluder manufactured by this method has better conformability and resilience and does not need to be assisted by the locking device to recover its original shape. After the implantation to the defect or abnormal site, the occluder can return to the original shape by the characteristics of its own material and structural design that is easy to recover. Then it is firmly fixed in the defect or abnormal site. It will greatly reduce the difficulty of doctor's operation. The structural design of this occluder of this invention can be retracted repeatedly, which is more conducive to the operation and adjustment in the surgery. If the occluder chosen at the outset is not suitable, it is very easy to retract the occluder to the delivery sheath and replace it with a suitable occluder to continue the procedure, which will greatly reduce the risk of surgery.

SUMMARY OF THE INVENTION

The technical problem to be solved by the invention is to solve the problem of the long-term risk of the existing clinically used occluder and to overcome the defect that the compliance and recovery of the degradable occluder are poor in the prior art and to provide a degradable occluder.

The present invention solves the above technical problems through the following technical solutions:

A degradable occluder is characterized in that it comprises a first disc-shaped mesh, a tubular mesh and a second disc-shaped mesh which are sequentially connected, two ends of the tubular mesh are respectively connected to the first disc-shaped mesh and the second disc-shaped mesh, wherein the first disc-shaped mesh, the tubular mesh, and the second disc-shaped mesh are integrally formed; the second disc-shaped mesh is provided with a connector used for closing a mesh surface, wherein the connector is formed by heat-melting the mesh body of the second disc-shaped mesh, the materials of the first disc-shaped mesh, the tubular mesh, the second disc-shaped mesh and the connector are all degradable materials. The occluder of the present invention is mainly used for the treatment of structural heart disease. Since the sizes and positions of defects or abnormalities in the heart are different, the sizes and shapes of occluders required are also different. There are mainly five types of occluders. The characteristics of the occluder are as follows.

Preferably, the degradable occluder is a degradable cardiac atrial septal defect occluder, wherein both the first disc-shaped mesh and the second disc-shaped mesh are double-layer mesh covers. The two ends of the tubular mesh are respectively connected to an inner mesh surface of the first disc-shaped mesh and an outer mesh surface of the second disc-shaped mesh; the connector is provided at a center of an inner mesh surface of the second disc-shaped mesh, wherein the connector is formed by heat-melting the mesh body at the center of the inner mesh surface of the second disc-shaped mesh.

Preferably, the degradable occluder is a degradable cardiac patent ductus arteriosus occluder, wherein the first disc-shaped mesh is a double-layer mesh cover and the second disc-shaped mesh is a single-layer mesh cover. Two ends of the tubular mesh are respectively connected to the inner mesh surface of the first disc-shaped mesh and the second disc-shaped mesh. The connector is provided at a center of the inner mesh surface of the second disc-shaped mesh wherein the connector is formed by heat-melting the mesh body at the center of the inner mesh surface of the second disc-shaped mesh.

Preferably, the degradable occluder is a degradable cardiac ventricular septal defect occluder, wherein the first disc-shaped mesh and the second disc-shaped mesh are double-layer mesh covers. The two ends of the tubular mesh are respectively connected to the inner mesh surface of the first disc-shaped mesh and the outer mesh surface of the second disc-shaped mesh. The connector is provided at a center of the inner mesh surface of the second disc-shaped mesh wherein the connector is formed by heat-melting the mesh body at the center of the inner mesh surface of the second disc-shaped mesh. The height of the tubular mesh is 3.5-9.5 mm.

Preferably, the degradable occluder is a degradable cardiac patent foramen ovale occluder wherein both the first disc-shaped mesh and the second disc-shaped mesh are double-layer mesh covers. Two ends of the tubular mesh are respectively connected to the inner mesh surface of the first disc-shaped mesh and the inner mesh surface of the second disc-shaped mesh. The connector is provided at a center of the outer mesh surface of the second disc-shaped mesh, wherein the connector is formed by heat-melting the mesh body at the center of the outer mesh surface of the second disc-shaped mesh. The outer mesh surface of the second disc-shaped mesh is convex toward the connector.

Preferably, the degradable occluder is a degradable heart left atrial appendage occluder, wherein the first disc-shaped mesh is a single-layer mesh cover and the second disc-shaped mesh is a double-layer mesh cover. Two ends of the tubular mesh are respectively connected to the first disc-shaped mesh and the outer mesh surface of the second disc-shaped mesh. The connector is provided at a center of the inner mesh surface of the second disc-shaped mesh, wherein the connector is formed by heat-melting the mesh body at the center of the inner mesh surface of the second disc-shaped mesh.

Preferably, the first disc-shaped mesh includes a closing end which is a plurality of sequentially adjoining ring mesh lines. The first disc-shaped mesh is further provided with a closing line which is passed through all of the ring mesh lines, wherein the outer surface of the first disc-shaped mesh forms a continuously flat mesh surface after being closed by the closing line. In this way, the outer mesh surface is flatter, the supporting force and recovery of the occluder can be increased, the risk of local thrombus formation on the surface of the occluder can be reduced, and the progress of endothelialization on the occluder surface can be accelerated so that the repair site can be earlier recovered by its own tissue. At the same time, the release length of the occluder during the operation is reduced, which can greatly reduce the damage to the heart and make the surgery more effective and safer.

Preferably, the connector is tubular and the height of the connector is 1.5-2.0 mm. In this way, the strength of the inner mesh surface of the second disc-shaped mesh at the closing end is sufficient. If the height of the connector is too small and the number of thread turns inside the connector is too less, the connection with the conveying system may be caused to be weak and there is a risk of the occluder falling off. Conversely, if the height of the connector is too large, the risk of local thrombus formation on the surface of the occluder will increase, it will slower cell climbing on the surface of the occluder at the side with the connector and will increase the endothelialization progress of the occluder surface. At the same time, the release length of the occluder is longer during the implantation procedure so that it is easy to damage the heart tissue.

Preferably, the outer diameter of the connector is 2.5-3.2 mm. In this way, the strength of the inner mesh surface of the second disc-shaped mesh at the closing end is sufficient. In addition, if the outer diameter of the connector is too small, it easily leads to the breakage or the decrease in connection strength of the degraded filament which is connected to the connector during the connector forming process. On the other hand, if the outer diameter of the connector is too large, the size range of the delivery sheath that the occluder is suitable for will be reduced and it will be unfavorable for the push of the occluder in the delivery sheath.

Preferably, the materials of the first disc-shaped mesh, the tubular mesh, the second disc-shaped mesh, and the connector are all macromolecule degradable filaments. The degradable polymer material is one kind of or copolymers of at least two kinds of polylactic acid, polyglycolic acid, polycaprolactone, polydioxanone, polyhydroxybutyrate, polyanhydride, polyphosphate, polyurethane, or polycarbonate. These materials have good biocompatibility and can be completely absorbed in the human body so that it avoids the long-term effects of implanted foreign bodies on the human body. This occluder only provides a temporary bridge for heart repair. After the completion of the historical mission, it is degraded by the body so that the defect is completely repaired by the self tissue. Thus it avoids the long-term complications and hidden dangers caused by metal retention.

Preferably, the connector is tubular, it is provided with an internal thread at an end opposite to the connected mesh surface. The connection to the delivery system is stronger by this screwed connector and the occluder can be conveniently transported to the heart defect or anomaly through the delivery system.

Preferably, the inner mesh surface of the first disc-shaped mesh is concave toward the tubular mesh and the inner mesh surface of the second disc-shaped mesh is concave toward the connector. The concave mesh surface can enable the occluder to stably and firmly block at the atrial septal defect.

Preferably, the outer diameter of the first disc-shaped mesh is 4-6 mm larger than the outer diameter of the second disc-shaped mesh. The first disc-shaped mesh is located in the left atrium of the heart, and the second disc-shaped mesh is located in the right atrium of the heart. The left atrial pressure in the heart is greater than the pressure in the right atrium so that the blood enters the right atrium from the left atrium by the atrial septal defect. So this structure makes the first disc-shaped mesh at the left atrium has a larger supporting force and can resist the impact of blood flow so that it is favorable for the occluder to firmly clamp at the atrial septal defect and achieve effective sealing.

Preferably, the outer diameter of the first disc-shaped mesh is 10-16 mm larger than the outer diameter of the tubular mesh. The diameter of the tubular mesh generally corresponds to the diameter of the atrial septal defect. The outer diameter of the first disc-shaped mesh needs to be larger than the outer diameter of the tubular mesh. This structure allows the first disc-shaped mesh in the left atrium to have a larger support force and able to resist the impact of blood flow so that it is conducive to clamp firmly at the atrial septal defect for the occluder and achieve effective sealing.

Preferably, the length of the tubular mesh is 3.5-5.5 mm. This length corresponds to the thickness of the atrial septal defect tissue so that the occluder is better fixed at the defect without damaging the tissue and effective sealing is achieved.

Preferably, the second disc-shaped mesh is concave toward the connector. The concave mesh surface can make the occluder have better elastic recovery after being released from the delivery sheath. Therefore, the occluder can stably and firmly seal the patent ductus arteriosus.

Preferably, the outer diameter of the first disc-shaped mesh is 5.5-6.5 mm greater than the outer diameter of the second disc-shaped mesh. The first disc-shaped mesh is located on the side of the aorta. The second disc-shaped mesh is located on the side of the pulmonary artery. For patients with patent ductus arteriosus, blood usually flows from the aorta to the pulmonary artery through the patent ductus arteriosus, so this structure allows the first disc-shaped mesh on the aorta side has a larger supporting force and can resist the impact of blood flow so that the occluder can be more firmly clamped at the patent ductus arteriosus and effective sealing can be achieved.

Preferably, the length of the tubular mesh is 4.5-6.5 mm. This length can be adapted to the length of the patent ductus arteriosus so that the occluder can be firmly clamped in the patent ductus arteriosus and effectively block the patent ductus arteriosus, and it will not affect the flow of blood in the pulmonary artery.

Preferably, the inner mesh surface of the second disc-shaped mesh is concave toward the connector. The concave mesh surface can enable the occluder to stably and firmly block the ventricular septal defect.

Preferably, the outer diameter of the first disc-shaped mesh is larger than or equal to the outer diameter of the second disc-shaped mesh. The first disc-shaped mesh is located in the left ventricle, and the second disc-shaped mesh is located in the right ventricle. Blood flows from the left ventricle to the right ventricle through the ventricular septal defect for patients with ventricular septal defect. This structure makes the first disc-shaped mesh at the left ventricle has a large supporting force and can resist the impact of blood flow, it is advantageous for the occluder to firmly clamp at the ventricular septal defect so that the ventricular septal defect can be effectively blocked. At the same time, it can avoid the restrictions to the surrounding tissues and reduce the damage to the surrounding tissues.

Preferably, the length of the tubular mesh is 3.5-5.5 mm. This length corresponds to the thickness of the defect tissue of the membranous part of ventricle septum so that the occluder can be better fixed at the defect without damaging the tissue and effective sealing can be achieved.

Preferably, the length of the tubular mesh is 6.0-9.5 mm. This length corresponds to the thickness of the septal defect tissue of the muscle part of ventricular septal so that the occluder can be better fixed at the defect without damaging the tissue and effective sealing can be achieved.

Preferably, the outer diameter of the second disc-shaped mesh is larger than or equal to the outer diameter of the first disc-shaped mesh. The first disc-shaped mesh is located in the left atrium and the second disc-shaped mesh is located in the right atrium. When the right atrial pressure is higher than the left atrial pressure, the left weaker primary septum is pushed open for patients with patent foramen ovale. The right-to-left shunt occurs. This structure allows the second disc-shaped mesh in the right atrium to have a larger supporting force, which can resist the impact of blood flow and facilitate the occluder to be firmly clamped in the patent foramen ovale. In this way, it can effectively block the foramen ovale.

Preferably, the inner mesh surface of the second disc-shaped mesh is concave toward the connector. The concave mesh surface can make that the occluder can stably and firmly seal the entrance of the heart left atrial appendage.

Preferably, the outer diameter of the second disc mesh is larger than the outer diameter of the first disc mesh. In this way, the second disc-shaped mesh positioned in the left atrium has a large supporting force, which can resist the impact of blood flow and can effectively block the entrance of the heart left atrial appendage.

A mesh tube weaving method includes inserting a pin into a pin hole of a mould bar, and threading a degradable filament into a needle hole of a sewing needle, and knotting and tightly connecting. Tightly knotting a starting point with degradable filaments, and aligning an intersection point between an up line and a down line with a central mark point when weaving, to regulate the direction of the filament. Heat-forming woven mesh tube with the mould bar. Removing the pin and getting the mesh tube after forming. This weaving method makes the mesh grid of the mesh tube more uniform, is easier to operate and reduces the production cost.

A method for making a connector includes the following steps:

step 1, closing one end of the mesh tube;
step 2, placing the mesh tube into a mould;
step 3, trimming a mesh body;
step 4, heating a degradable filament;
step 5, forming an outer shape and an internal thread of the connector;
step 6, removing the mesh body.

Preferably, in step 1, lengths of edges of the closing end of the mesh tube are adjusted so that the edges are aligned, and the one end is closed by the degradable filament.

Preferably, in step 2, a closed mesh tube is passed through a sleeve in the mould.

Preferably, in step 3, a part of an original assembly length is used to make the connector, and an excess length of the mesh tube is removed.

Preferably, in step 4, a temperature control device is opened to adjust temperature, and the degradable filament at the connector is continuously heated by heat above the mould, wherein the temperature is adjusted to be 40° C.-100° C. higher than a polymer melting point for heating 5-15 seconds. During the heating process, overheating will cause the other parts of the mesh body to fuse together, which results in the destruction of the mesh body structure and greatly reduction of the material molecular weight of the connector part so that it will cause the material to be premature degraded. On the contrary, insufficient heating will not cause the degradable filaments at the connector to be fully melted into one body and form a complete internal thread structure of the connector, which results in insufficient connection strength between the connector and the delivery system. Therefore, the proper heating temperature and time are required to complete the hot melting.

Preferably, in step 5, degradable filaments of the connector part are fused together after continuous heating, the temperature control device is removed, and then a slider in the mould is closed, and inserting a thread head of the mould into a slot above the mould for a period of time.

Preferably, in step 6, after cooling, the thread head of the mould is rotated out of the mould, and the slider is slowly removed, and the mesh body is removed from the mould.

The method for manufacturing the connector is easy to operate and stable dimension of connector can be obtained. In addition, the types of materials used on the occluder can be reduced so that the degradable filaments constituting the disc-shaped mesh can be firmly connected together. Also, the connector and the degradable filaments constituting the disc-shaped mesh can be firmly connected together wherein they do not easily fall off.

A mesh body forming method comprises: loading a mesh body with a connector into a mesh body forming mould, and using a jig to fix it and heat-forming it together, and after forming, removing the mesh body from the mould. Filling a degradable membrane into the mesh body with a suture, and closing the closing end to form a flat disc surface. The mesh body forming method is easy to operate and the size of the manufactured occluder is stable so that the occluder made by the method has larger supporting force and better shape recovery which meets the requirements of the surgical operation and makes the operation more effective and safer.

The positive and progressive effect of the present invention lies in:

The occluder of the present invention is formed by weaving macromolecule degradable filaments and its degradation cycle is from 6 months to 2 years, it can be completely absorbed in the human body thus avoid the long-term impact of implanting foreign substances on the human body. The macromolecule degradable filaments used in the present invention are a degradable or human-absorbable material that is non-toxic and harmless to the human body and has good biocompatibility. The obstruction membrane of the occluder is a degradable membrane and its degradation cycle is 6 months to 2 years. It degrades and disappears in the body and leaves no residual foreign matter after it completes its therapeutic mission in the human body.

The mesh body at the center of the second disc mesh is welded to be the connector by high-temperature hot-melt welding. Specifically, the mesh body at the center of the second disc-shaped mesh is heat-melted at a high temperature, and the hot-melt portion of mesh is formed into a connector by a mould so that the degradable filaments constituting the disc-shaped mesh are not easily scattered and can be firmly connected together. At the same time, the connector and the degradable filaments constituting the disc-shaped mesh can be firmly connected together and are not easy to fall off. The mesh surface without connector adopts the closing structure of closing line to make the outer mesh surface more smooth, which can reduce the risk of local thrombus formation on the surface of the occluder and accelerate the process of endothelialization of the occluder surface and make the defect recover by itself tissue early. At the same time, the released length of the occluder during surgery is reduced so it can greatly reduce the damage to the heart and make surgery more effective and safer. The occluder made by this method has better compliance and resilience which does not need the locking device to assist it return to its original shape. After being implanted in a defect or anomaly, the occluder can restore its original shape by virtue of its own material properties and easy-to-revert structural design, thereby the occluder can be firmly fixed in the defect or abnormal position, which will greatly reduce the difficulty of the doctor's intraoperative operation. The structure design of the occluder of this invention can be repeatedly retracted, which is more conducive to intraoperative operation and adjustment. If the occluder selected at the beginning is not suitably, the occluder can be easily retracted to the delivery sheath and replaced with a suitable type of occluder to continue the procedure, which will greatly reduce the surgical risk. In addition, the occluder also has the advantage of relatively low manufacturing costs.

DETAILED DESCRIPTION OF THE INVENTION

Embodiment 1

Figure 1:
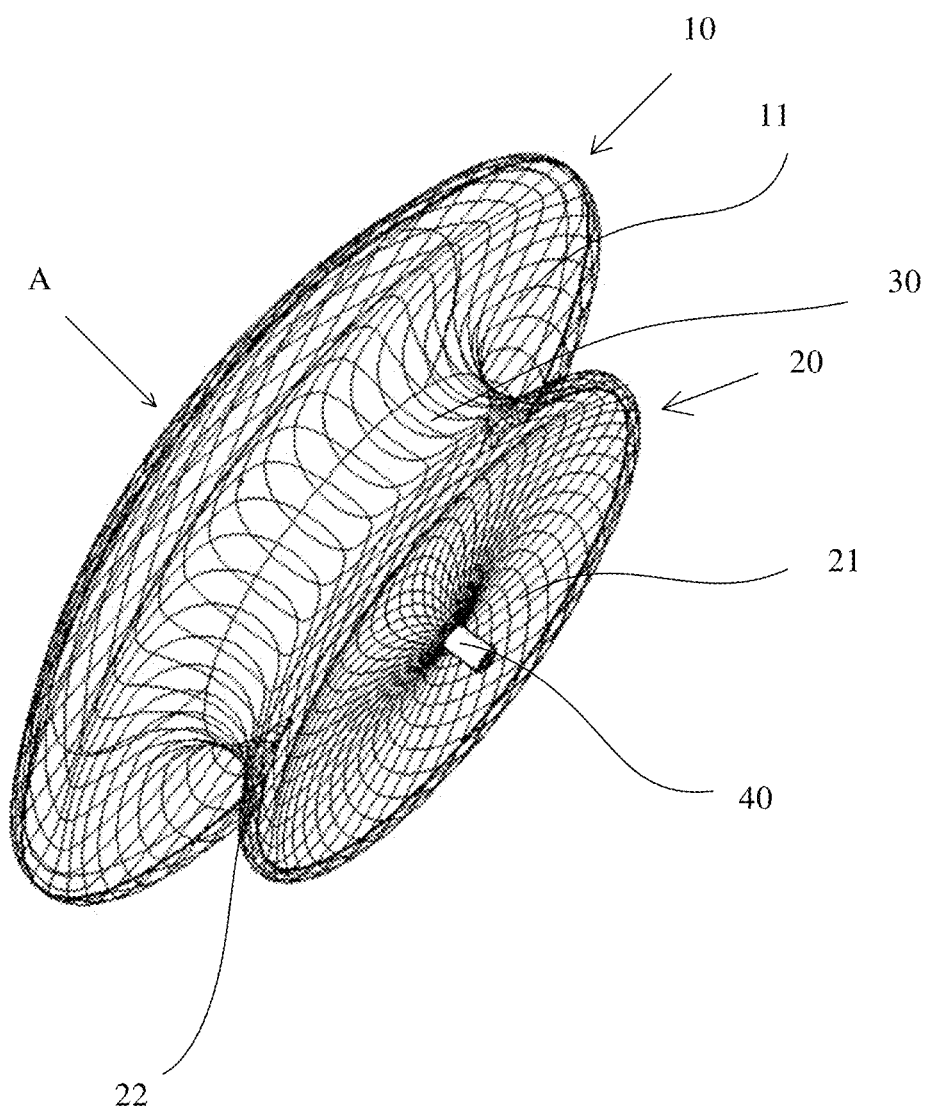
FIG. 1 is a schematic diagram of a three-dimensional structure of an occluder according to Embodiment 1.
Figure 2:
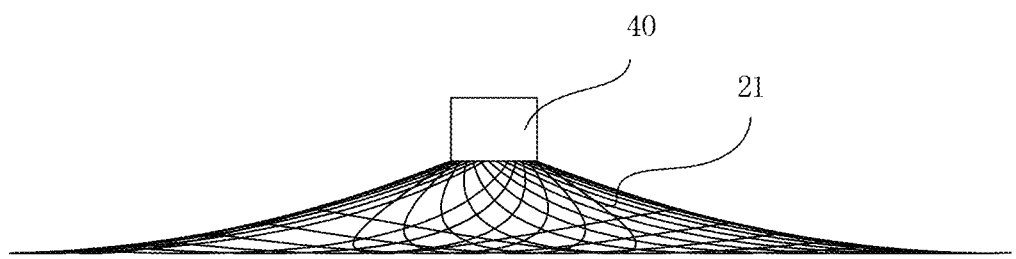
FIG. 2 is a schematic view of an occluder connector of Embodiment 1.
Figure 3:
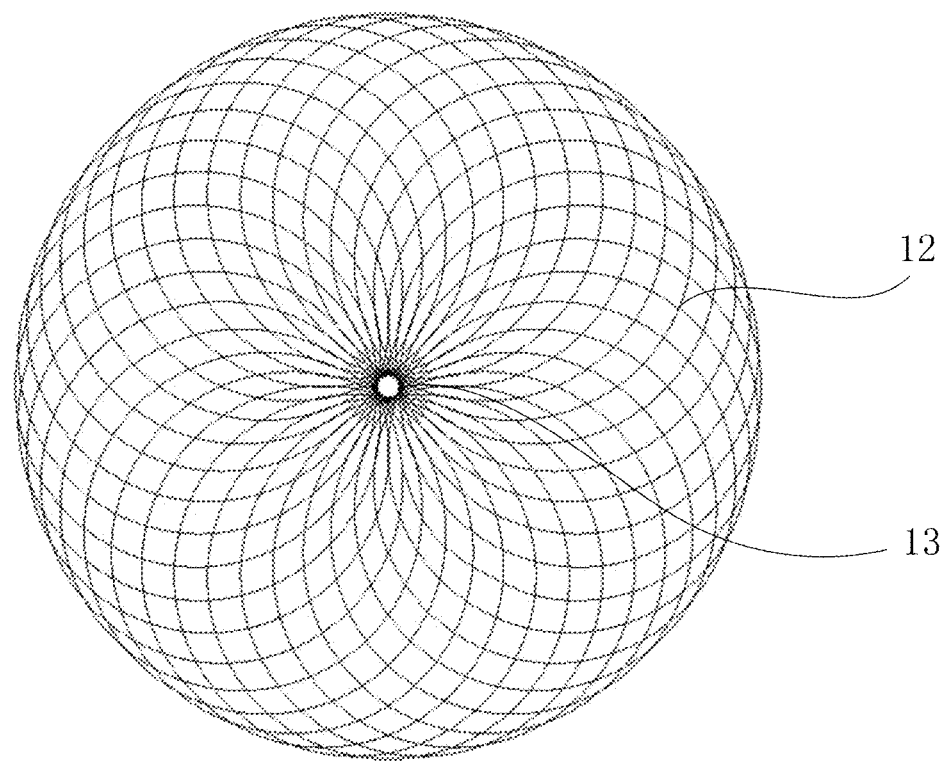
FIG. 3 is a view of A direction of FIG. 1.
Figure 4:
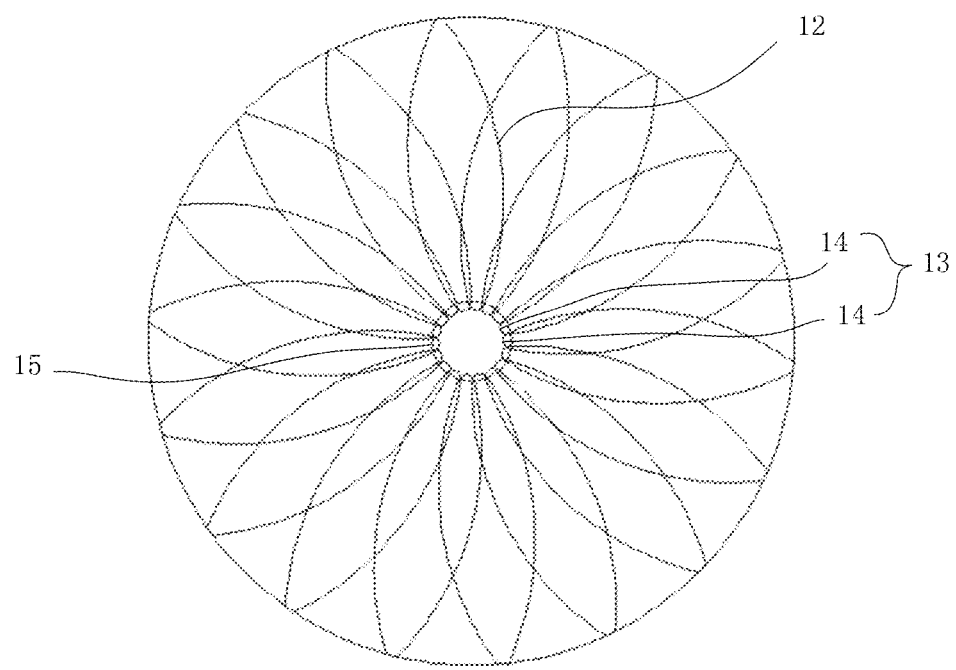
FIG. 4 is a partially enlarged schematic view of the outer mesh surface of the first disc-shaped mesh at the closing end in Embodiment 1.

As shown in FIG. 1, FIG. 2, FIG. 3 and FIG. 4, a degradable cardiac atrial septal defect occluder includes a first disc-shaped mesh 10, a tubular mesh 30, and a second disc-shaped mesh 20 which are sequentially connected. The first disc-shaped mesh 10 and the second disc-shaped mesh 20 are double-layer mesh covers. The two ends of the tubular mesh 30 are connected to the inner mesh surface 11 of the first disc-shaped mesh 10 and the outer mesh surface 22 of the second disc-shaped mesh 20 respectively. The first disc-shaped mesh 10, the tubular mesh 30, and the second disc-shaped mesh 20 are integrally formed. The center portion of the inner mesh surface 21 of the second disc-shaped mesh 20 is provided with a connector 40 that closes the mesh surface. The inner mesh surface 21 of the second disc-shaped mesh 20 is connected with the connector 40 by hot melt welding. The outer mesh surface 12 of the first disc-shaped mesh 10 includes a closing end 13, the closing end 13 is a plurality of consecutively adjacent ring mesh lines 14. The first disc-shaped mesh 10 is further provided with a closing line 15, the closing line 15 is passed through all the ring mesh lines 14. The outer mesh surface 12 of the first disc-shaped mesh 10 forms a continuous mesh surface after being closed by the closing line 15. The materials of the first disc-shaped mesh 10, the tubular mesh 30, the second disc-shaped mesh 20 and the connector 40 are all degradable materials.

In the present invention of the occluder, the mesh body at the center of the inner mesh surface of the second disc-shaped mesh 20 is welded by high temperature heat welding as a connector. Specifically, the mesh body at the center of the inner mesh surface of the second disc-shaped mesh 20 is heat-melted at a high temperature and the hot-melted portion mesh body is shaped into the connector 40 by using a mould so that the degradable filaments constituting the disc-shaped mesh are not easily dispersed and can be firmly connected together. At the same time, the connector 40 and the degradable filaments that make up the disc-shaped mesh can be firmly connected wherein they do not easily fall off.

The connector 40 is tubular, having a height of 1.5-2.0 mm and an outer diameter of 2.5-3.2 mm. The inner mesh surface 11 of the first disc-shaped mesh 10 is concave toward the tubular mesh 30 and the inner mesh surface 21 of the second disc-shaped mesh 20 is concave toward the connector 40. The outer diameter of the first disc-shaped mesh 10 is 4-6 mm greater than the outer diameter of the second disc-shaped mesh 20. The outer diameter of the first disc-shaped mesh 10 is 10-16 mm larger than the outer diameter of the tubular mesh 30. The length of the tubular mesh 30 is 3.5-5.5 mm. The connector 40 is tubular wherein it is provided with an internal thread at an end opposite to the connected mesh surface 21.

The materials of the first disc-shaped mesh 10, the tubular mesh 30, the second disc-shaped mesh 20 and the connector 40 are all macromolecule degradable filaments. The degradable polymer material is one kind of or copolymers of at least two kinds of polylactic acid, polyglycolic acid, polycaprolactone, polydioxanone, polyhydroxybutyrate, polyanhydride, polyphosphate, polyurethane or polycarbonate. The occluder can be filled with polylactic acid film to block the blood flow.

The connector of the present invention is made through melting the degradable filaments and needs to meet the use conditions. Not only the structure cannot be so large that it prevents the pushing of the occluder in the delivery sheath, but also it is required to avoid pulling off of the connector due to insufficient connection strength.

TABLE 1

Test table of connector size, resistance force to pull-off and push in the delivery sheath

| | Height/mm | Outer diameter/mm | Resistance force to pull-off/N | Push in the delivery sheath |
| --- | --- | --- | --- | --- |
| 1 | 2.0 | 1.8 | 6 (weak) | unhindered |
| 2 | 2.0 | 2.0 | 11 (weak) | unhindered |
| 3 | 2.0 | 2.5 | 25 (strong) | unhindered |
| 4 | 1.5 | 2.5 | 20 (strong) | unhindered |
| 5 | 1.8 | 2.8 | 31 (strong) | unhindered |
| 6 | 1.5 | 3.0 | 34 (strong) | unhindered |
| 7 | 2.0 | 3.2 | 41 (strong) | unhindered |
| 8 | 2.0 | 3.5 | 52 (strong) | hindered |

It was found in the test that when the resistance force to pull-off reached 15N, it was guaranteed that the connector would not be pulled off during use. According to the above table 1, it can be seen that the size of the connector directly affects whether the occluder can be properly used in the operation. Improper size design of the connector can result in the connector being pulled off or unable to enter the delivery sheath for pushing, which can render the product unusable.

The first disc-shaped mesh of the occluder is a continuous mesh surface and a closing line is used to close the mesh lines of the first mesh so that the first external disc-shaped mesh has a flat and smooth mesh surface without protrusions, and the structure is beneficial to improve the shape recovery and support force, it is also conducive to accelerate the process of endothelialization of the occluder surface so that the heart defect is repaired by its own tissue earlier. In the occluder of the present invention, the mesh body at the center of the inner mesh surface of the second disc-shaped mesh is welded and formed a connector by high-temperature hot-melt welding. Specifically, the mesh body at the center of the inner mesh surface of the second disc-shaped mesh is welded by high-temperature hot-melt welding and a mould is used to make the hot-melt portion of the mesh body into a connector, so that the degradable filaments constituting the disc-shaped mesh are not easily dispersed and can be firmly connected together; at the same time, the connector and the degradable filaments constituting the disc-shaped mesh can be firmly connected and do not easily peel off.

The occluder of the invention is mainly manufactured through the steps of forming a mesh tube, making a connector, shaping the mesh body and sewing the polylactic acid film.

Figure 5:
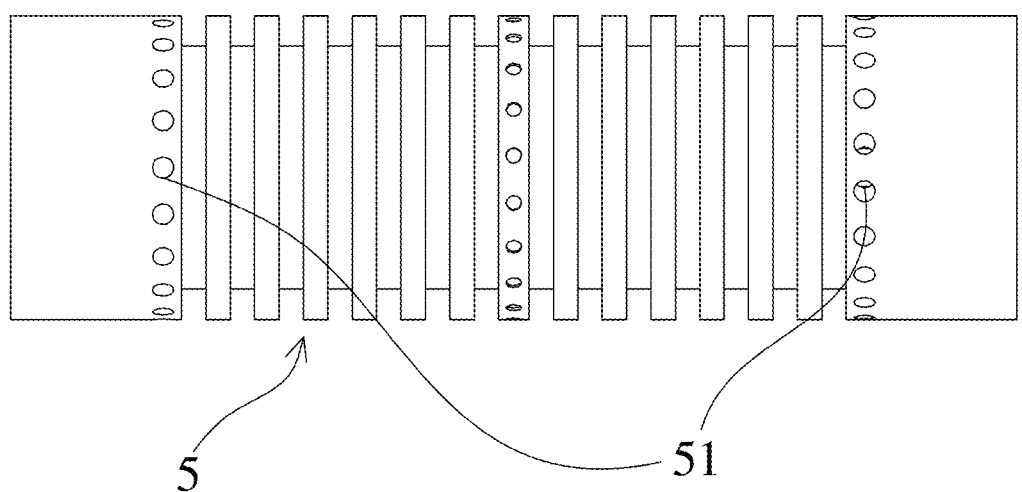
FIG. 5 is a schematic view of a mould bar of Embodiment 1.
Figure 6:
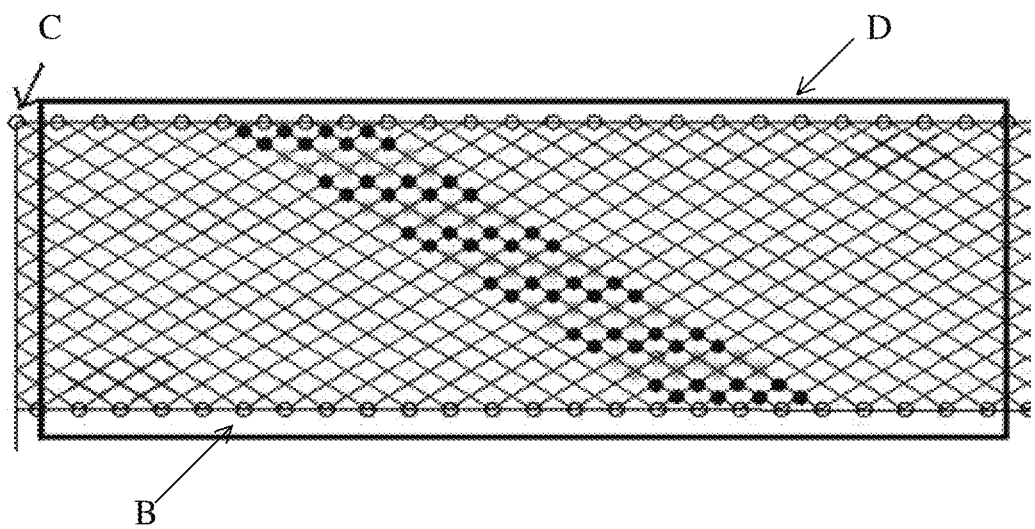
FIG. 6 is a schematic view of a weaving and threading of a mesh tube of Embodiment 1.

When the mesh tube is woven, the pin is inserted into the pin hole 51 of the mould bar 5 in FIG. 5. The degradable filament is threaded into the pin hole of the sewing needle wherein it is knotted and tightly connected. The threading pattern of weaving is shown in FIG. 6 wherein it includes a producing end D of connector, a closing end B (the receiving end 13 after forming) and a starting point C. The starting point C is tightly knotted with degradable filaments, and the intersection point between the up line and the down line is aligned with the central mark point when weaving to regulate the direction of the filament. The woven mesh tube is heat-formed with the mould bar. After heat forming, removing the pin and getting the mesh tube.

Figure 7:
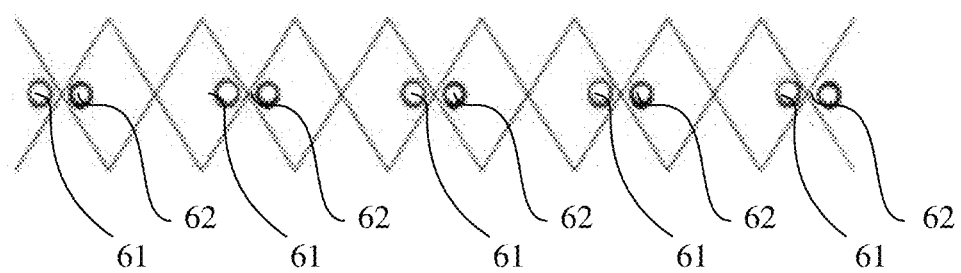
FIG. 7 is a schematic view of the deployment of the mesh tube at the closing end according to Embodiment 1.
Figure 8:
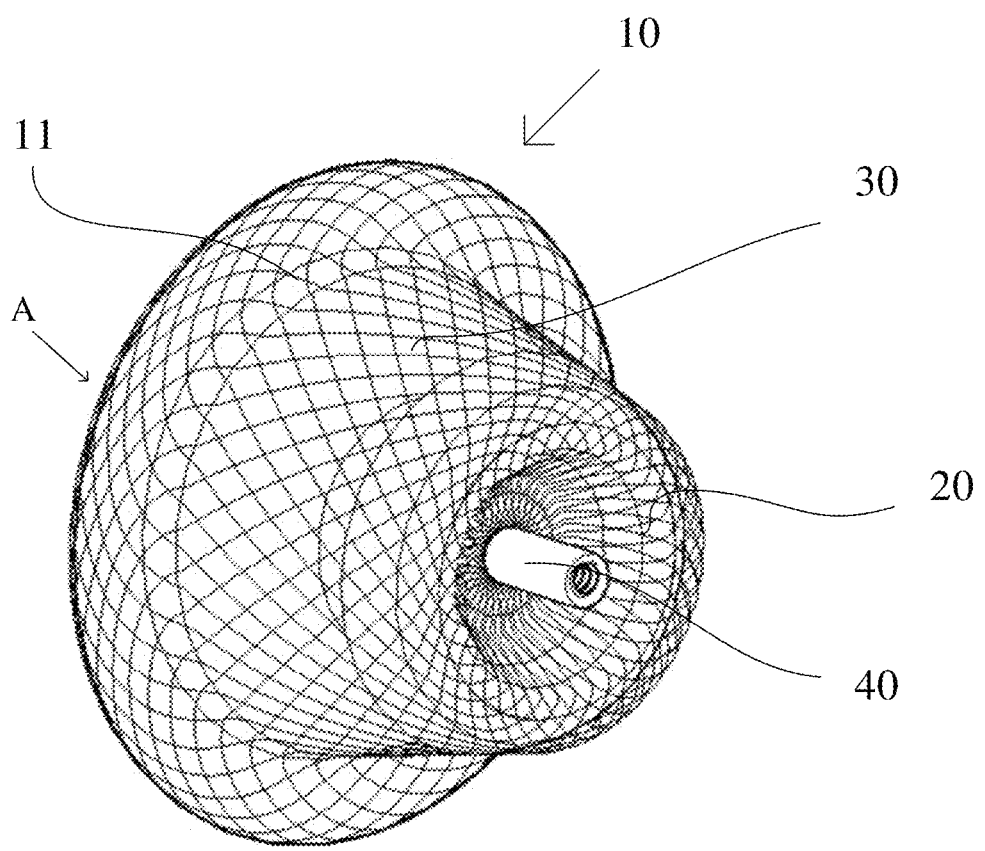
FIG. 8 is a schematic diagram of a three-dimensional structure of an occluder according to Embodiment 2.
Figure 9:
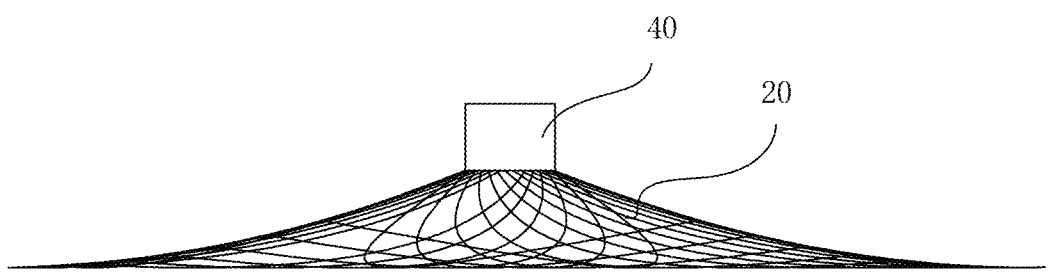
FIG. 9 is a schematic view of an occluder connector according to Embodiment 2.
Figure 10:
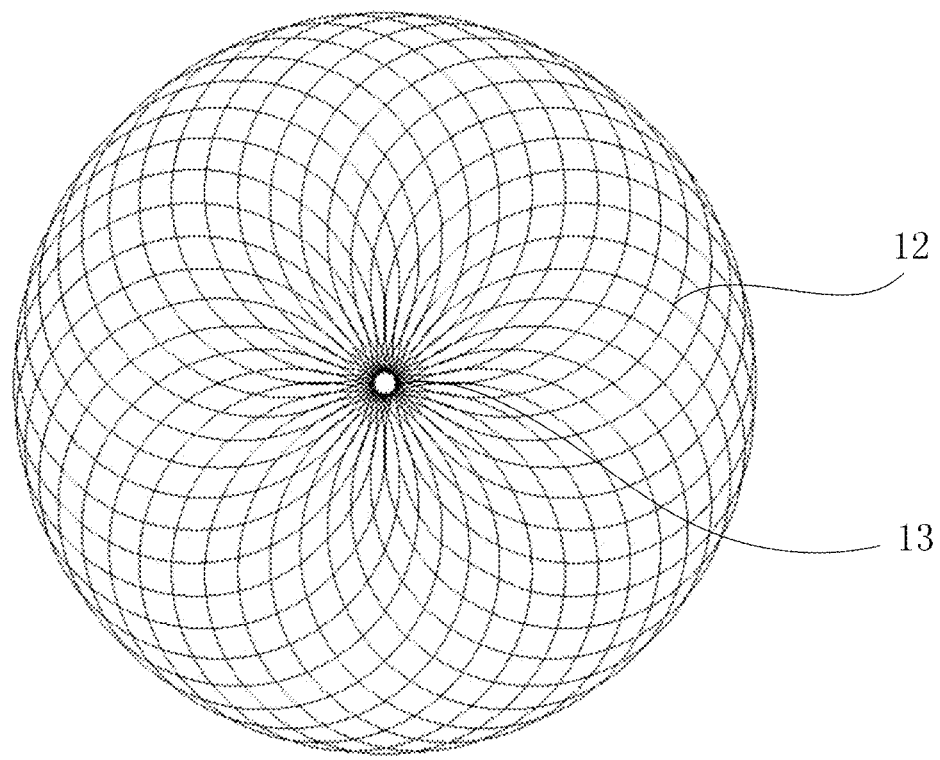
FIG. 10 is a view of direction A of FIG. 8.
Figure 11:
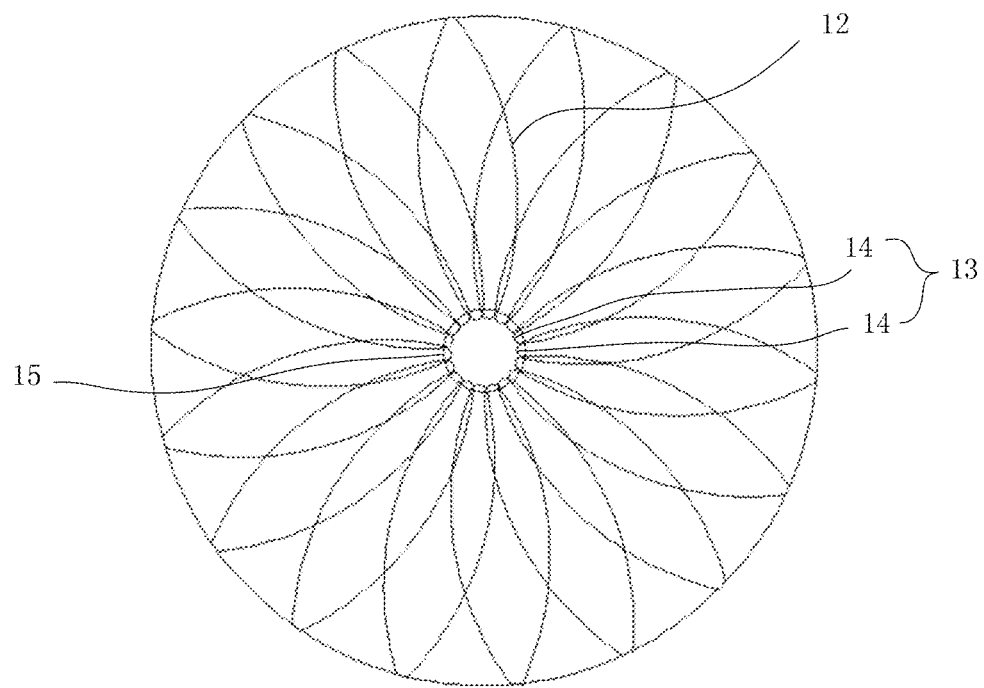
FIG. 11 is a partial enlarged schematic view of the closing end of the outer mesh surface of the first disc-shaped mesh in Embodiment 2.
Figure 12:
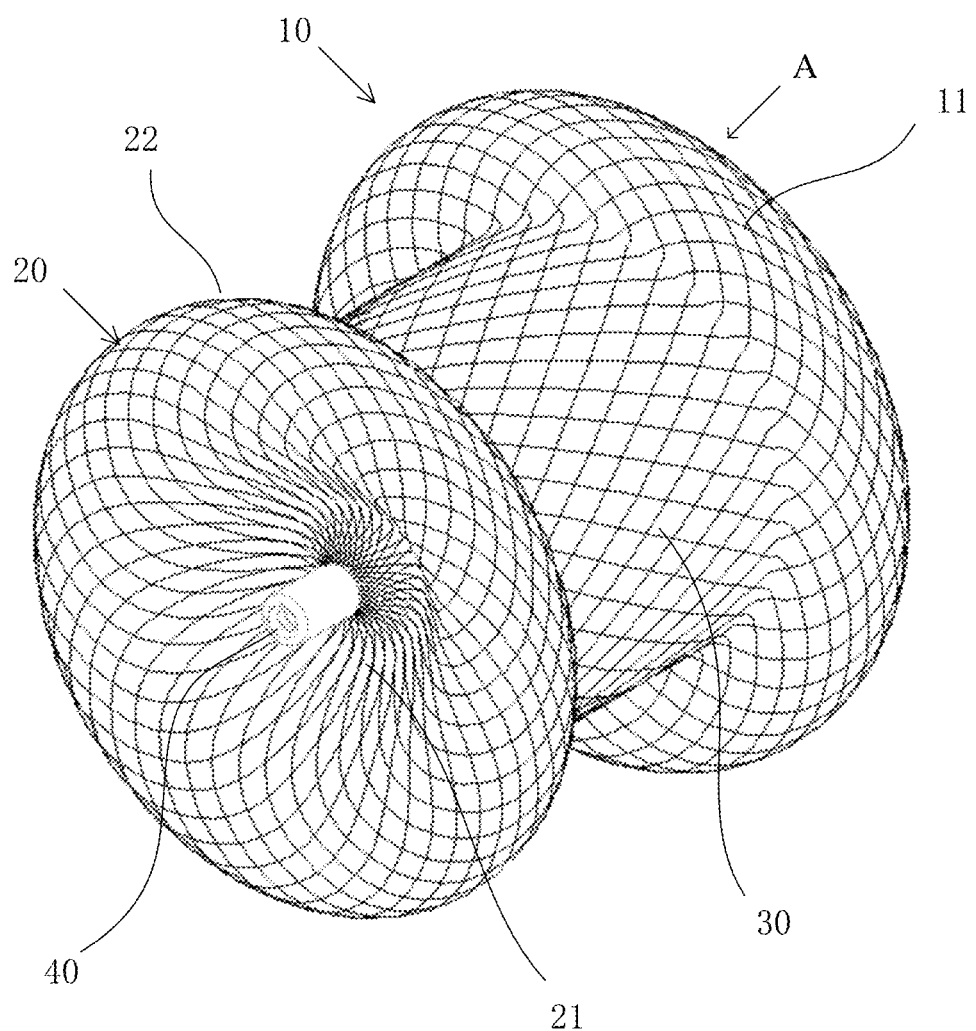
FIG. 12 is a schematic view of a three-dimensional structure of an occluder of Embodiment 3.
Figure 13:
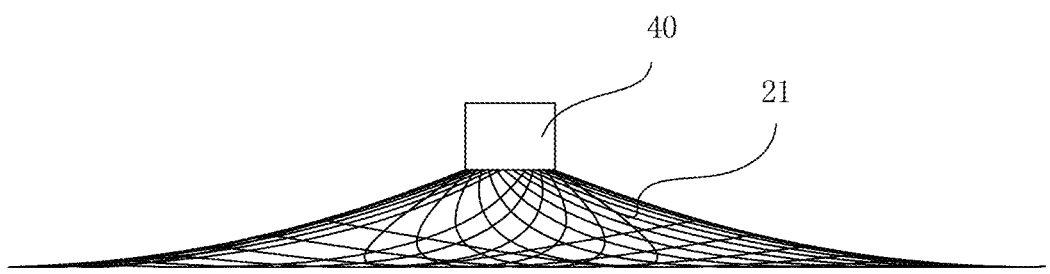
FIG. 13 is a schematic view of an occluder connector of Embodiment 3.
Figure 14:
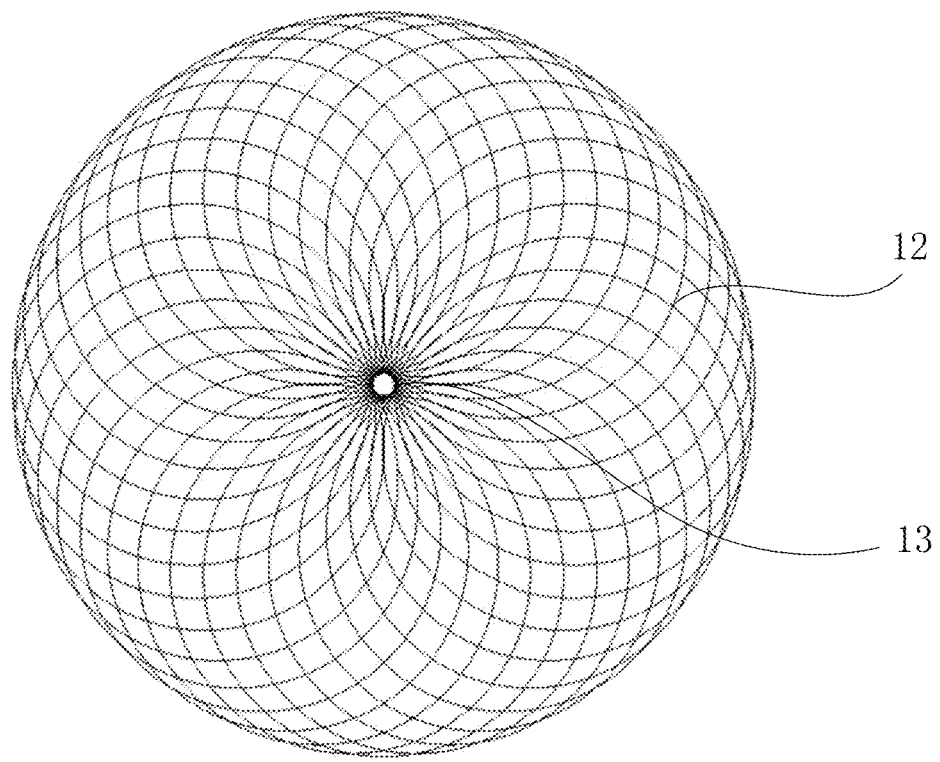
FIG. 14 is a view of A direction of FIG. 12.
Figure 15:
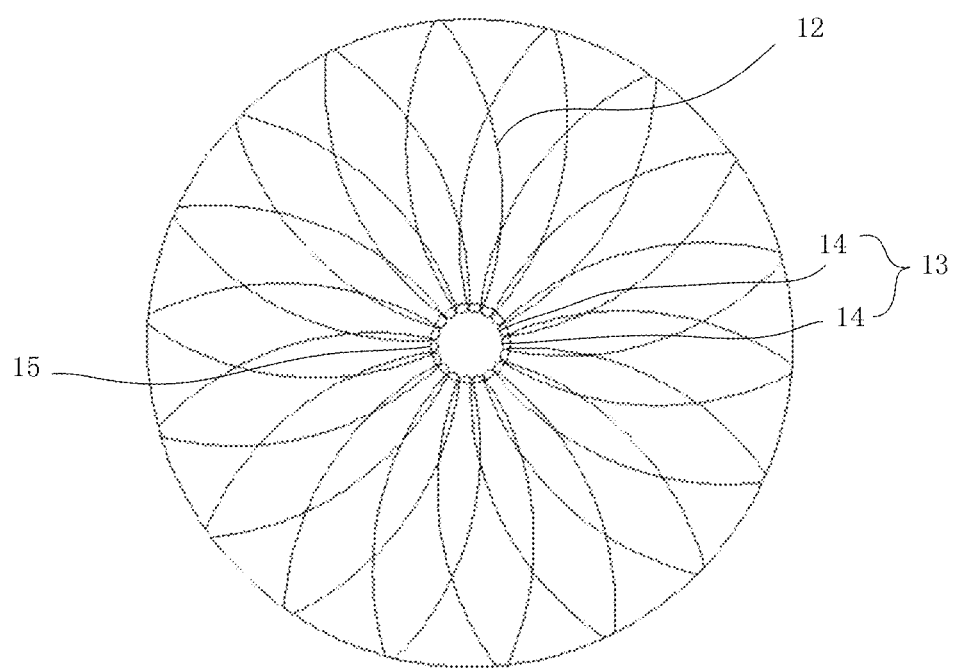
FIG. 15 is a partially enlarged schematic view of a closing end of an outer mesh surface of a first disc-shaped mesh in Embodiment 3.
Figure 16:
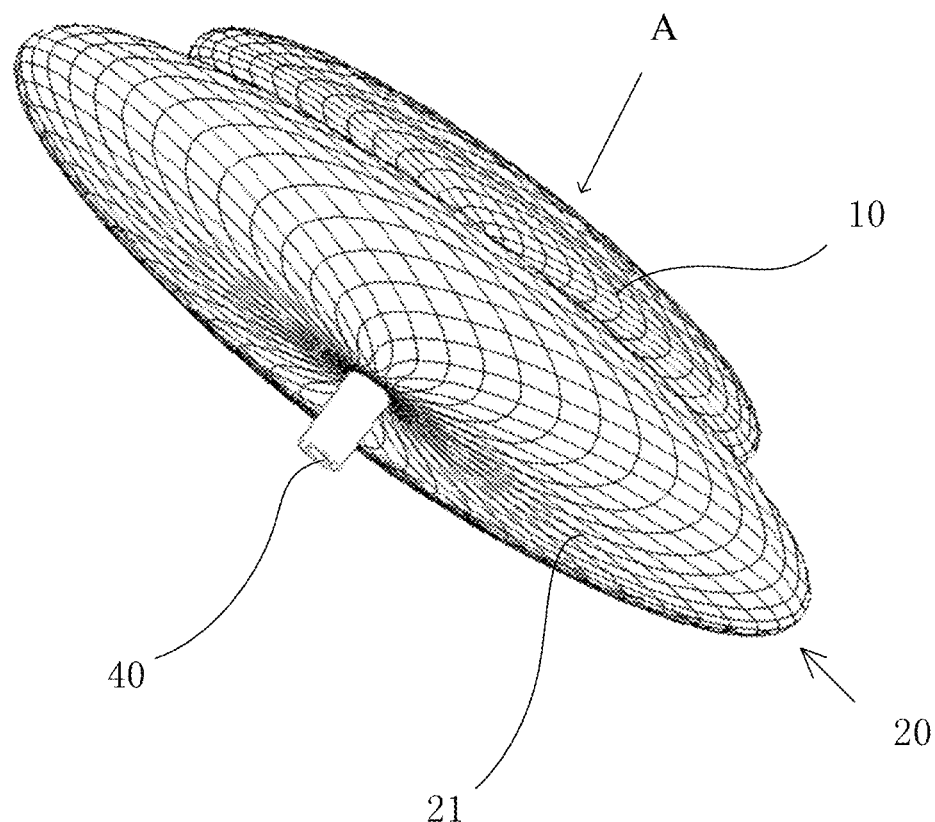
FIG. 16 is a schematic perspective view of a three-dimensional structure of the occluder of according to Embodiment 4.
Figure 17:
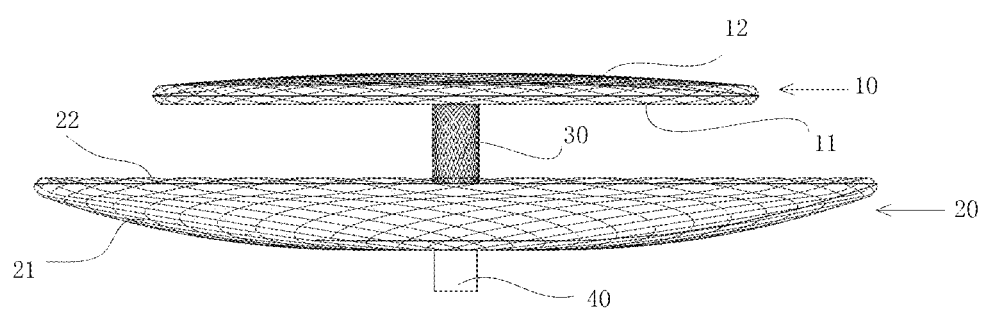
FIG. 17 is a schematic view of a side portion of an occluder according to Embodiment 4. FIG.
Figure 18:
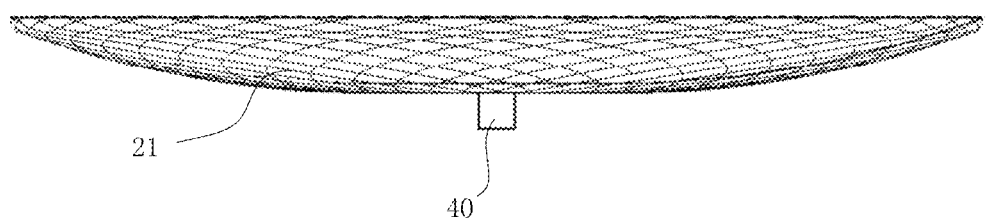
FIG. 18 is a schematic view of an occluder connector according to Embodiment 4.
Figure 19:
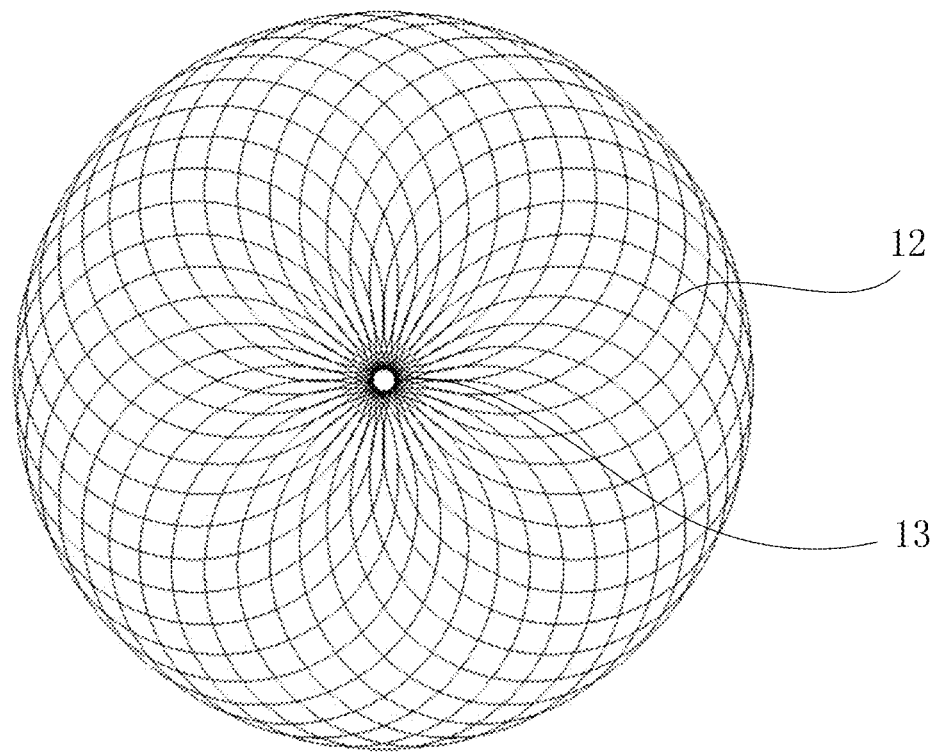
FIG. 19 is a view of A direction of FIG. 16.
Figure 20:
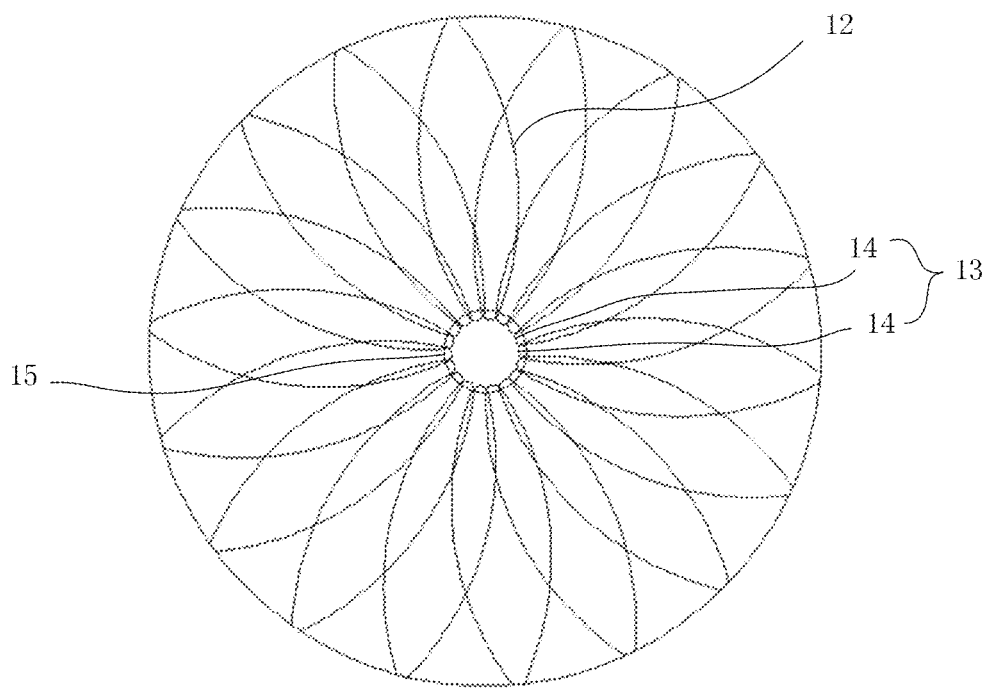
FIG. 20 is a partially enlarged schematic view of the closing end of the outer mesh surface of the first disc-shaped mesh in Embodiment 4.
Figure 21:
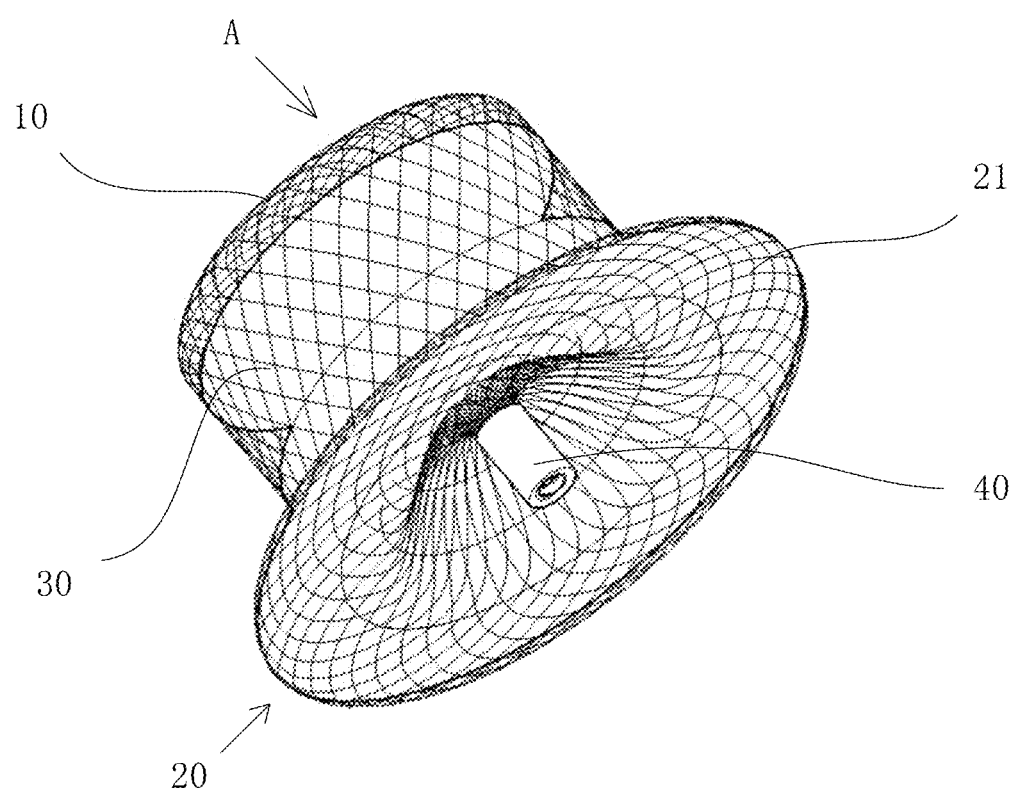
FIG. 21 is a schematic view of a three-dimensional structure of the occluder according to Embodiment 5.
Figure 22:
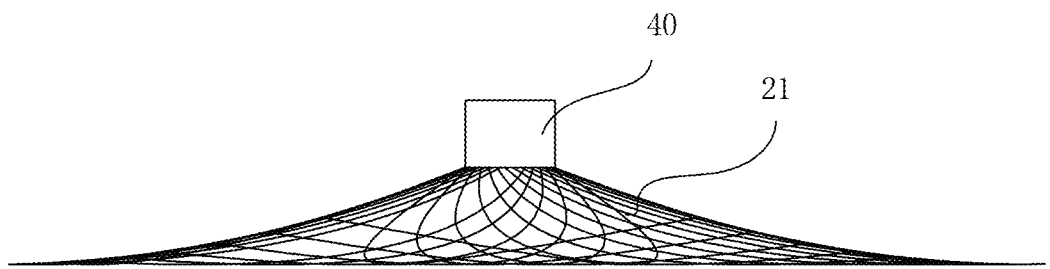
FIG. 22 is a schematic view of an occluder connector according to Embodiment 5.
Figure 23:
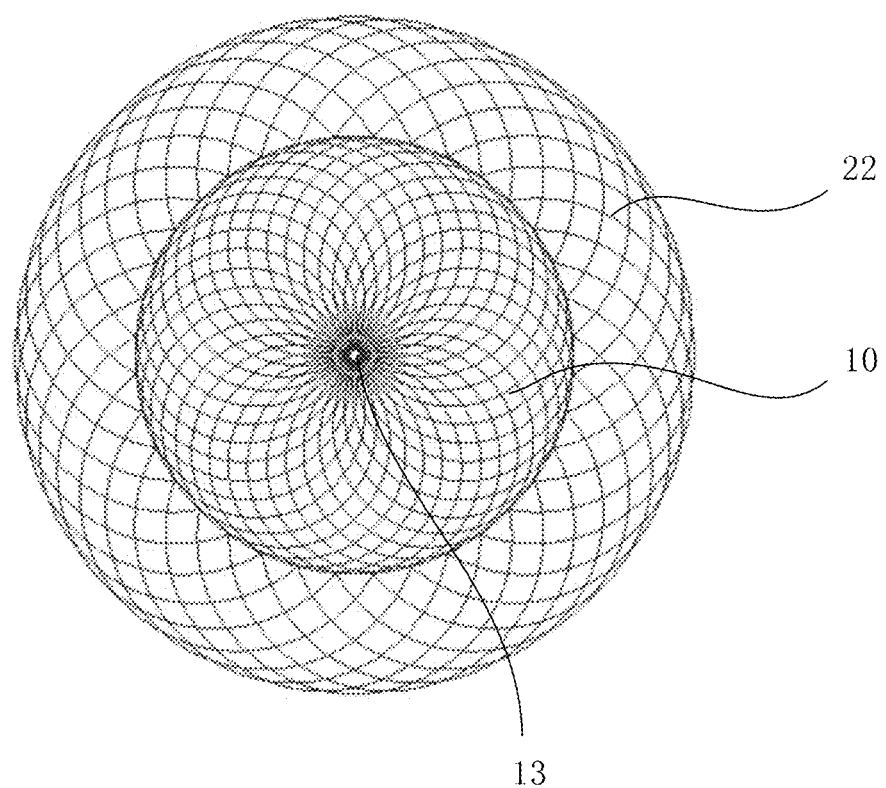
FIG. 23 is a view of A direction of FIG. 21
Figure 24:
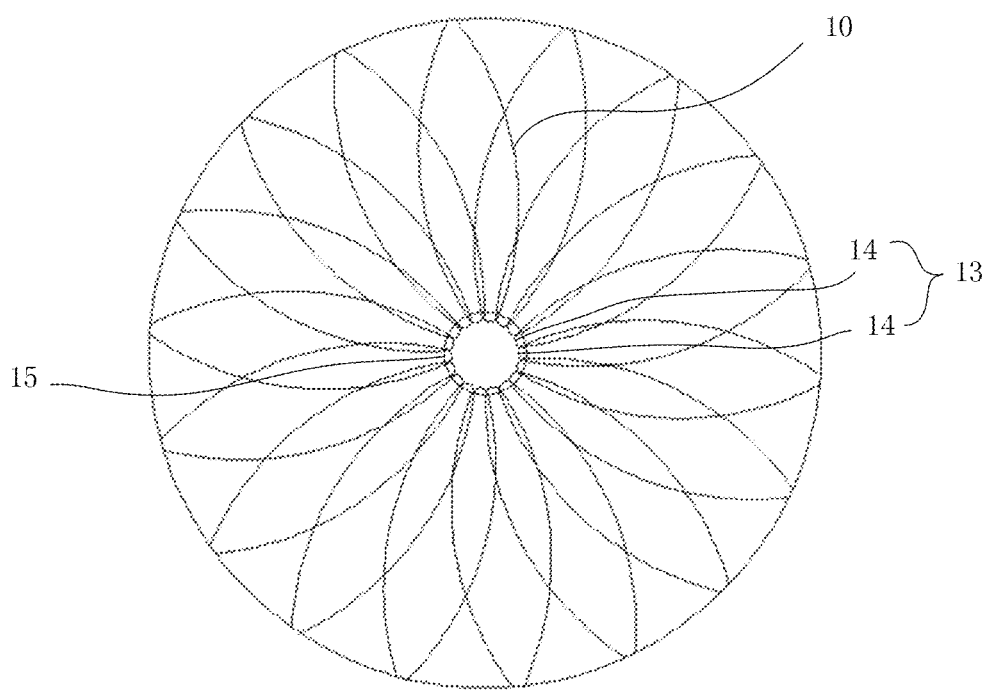
FIG. 24 is a partial enlarged schematic view of the closing end of the first disc-shaped mesh in Embodiment 5.

The manufacturing steps of connector include:
1, closing one end of the mesh tube;
2, placing the mesh tube into the mould;
3, trimming the mesh body;
4, heating degradable filaments;
5, forming outer shape and internal thread of the connector;
6, removing the mesh body out of the mould.

Wherein in step 1, lengths of the closing end edges of the mesh tube are adjusted so that the edges are aligned and it is closed by the degradable filament. The specific closing method is shown in FIG. 7, which includes the needle exit point 61 and the needle insertion point 62, and the end is closed through the threading sequence according to the needle exit point 61 and the needle insertion point 62 in FIG. 7. In step 2, the closed mesh tube is passed through the sleeve in the mould. In step 3, a portion of the original assemble length of the mesh tube is left to make the connector and the excess length of the mesh tube is removed. In step 4, the temperature control device is turned on to adjust the temperature wherein the degradable filament at the connector is continuously heated by heat above the mould. In step 5, after the continuous heating, the degradable filaments of the connector part are fused together and the temperature control device is removed. Then, the slider in the mould is closed and the thread head of the mould is inserted into the slot above the mould for a period of time. In step 6, after cooling, the thread head of the mould is rotated out of the mould and the slider is slowly removed, and the mesh body is removed from the mould.

In addition, in step 4 the temperature is adjusted to be 40° C.-100° C. higher than the melting point of the polymer and maintain 5-15 seconds. As shown in Tables 2 to 4 below, during the heating process, overheating causes the other parts of the mesh body to fuse together which results in the destruction of the mesh structure. The material molecular weight of the connector part is also greatly reduced which causes the material to degrade prematurely. On the contrary, insufficient heating will not cause the degradable filaments at the connector to be fully melted into one body and to form a complete internal thread structure of the connector, which results in insufficient connection strength between the connector and the delivery system. Therefore, the proper heating temperature and time are required to complete the hot melting.

TABLE 2

Hot melting test table of L-lactide/glycolide (82/18) degradable material

| | Heat time/s | Heat temperature/° C. | Hot melting condition of connector | Hot melting condition of other parts |
|---|---|---|---|---|
| 1 | 2 | 240 | Not fully hot-melted | Not hot-melted |
| 2 | 15 | 170 | Not fully hot-melted | Not hot-melted |
| 3 | 5 | 240 | fully hot-melted | Not hot-melted |
| 4 | 5 | 180 | fully hot-melted | Not hot-melted |
| 5 | 15 | 240 | fully hot-melted | Not hot-melted |
| 6 | 15 | 180 | fully hot-melted | Not hot-melted |
| 7 | 5 | 250 | fully hot-melted | Partially hot-melted |
| 8 | 20 | 180 | fully hot-melted | Partially hot-melted |

TABLE 3

Hot melting test table of polydioxanone degradable material

| | Heat time/s | Heat temperature/° C. | Hot melting condition of connector | Hot melting condition of other parts |
|---|---|---|---|---|
| 1 | 2 | 200 | Not fully hot-melted | Not hot-melted |
| 2 | 15 | 130 | Not fully hot-melted | Not hot-melted |
| 3 | 5 | 200 | fully hot-melted | Not hot-melted |
| 4 | 5 | 140 | fully hot-melted | Not hot-melted |
| 5 | 15 | 200 | fully hot-melted | Not hot-melted |
| 6 | 15 | 140 | fully hot-melted | Not hot-melted |
| 7 | 5 | 210 | fully hot-melted | Partially hot-melted |
| 8 | 20 | 140 | fully hot-melted | Partially hot-melted |

TABLE 4

Hot melting test table of L-lactide/caprolactone (70/30) degradable material

| | Heat time/s | Heat temperature/° C. | Hot melting condition of connector | Hot melting condition of other parts |
|---|---|---|---|---|
| 1 | 2 | 210 | Not fully hot-melted | Not hot-melted |
| 2 | 15 | 140 | Not fully hot-melted | Not hot-melted |
| 3 | 5 | 210 | fully hot-melted | Not hot-melted |
| 4 | 5 | 150 | fully hot-melted | Not hot-melted |
| 5 | 15 | 210 | fully hot-melted | Not hot-melted |
| 6 | 15 | 150 | fully hot-melted | Not hot-melted |
| 7 | 5 | 220 | fully hot-melted | Partially hot-melted |
| 8 | 20 | 150 | fully hot-melted | Partially hot-melted |

The mesh body forming includes putting the mesh body in the mould and its heat forming. When the mesh body is put in the mould, the aforementioned mesh body with the connector is loaded into the mesh body forming mould and fixed with a jig, and heat forming together. After the forming is completed, the mesh body is taken out from the mould. The polylactic acid film is filled into the mesh body with a suture, and closing the closing end to form a flat disc surface.

Embodiment 2

As shown in FIG. 8, FIG. 9, FIG. 10 and FIG. 11, a degradable heart patent ductus arteriosus occluder comprises a first disc-shaped mesh 10, a tubular mesh 30 and a second disc-shaped mesh 20 which are sequentially connected. The first disc-shaped mesh 10 is a double-layer mesh cover and the second disc-shaped mesh 20 is a single-layer mesh cover. Both ends of the tubular mesh 30 are respectively connected to the internal mesh surface 11 of the first disc-shaped mesh 10 and the second disc-shaped mesh 20.

The first disc-shaped mesh 10, the tubular mesh 30 and the second disc-shaped mesh 20 are integrally formed. The center of the second disc-shaped mesh 20 is provided with a connector 40 that closes the mesh surface. The connection between the second disc-shaped mesh 20 and the connector 40 is a hot-melt welding connection. The outer mesh surface 12 of the first disc-shaped mesh 10 includes a closing end 13 wherein the closing end 13 is a plurality of sequentially adjacent ring mesh lines 14. The first disc-shaped mesh 10 is also provided with a closing line 15 wherein the closing line 15 is passed through all the ring mesh lines 14. The outer mesh surface 12 of the first disc-shaped mesh 10 forms a continuous mesh after being closed by the closing line 15. The materials of the first disc-shaped mesh 10, the tubular mesh 30, the second disc-shaped mesh 20 and the connector 40 are all degradable materials.

In the present invention of the occluder, the mesh body at the center of the second disc-shaped mesh 20 is welded by high temperature heat welding as a connector. Specifically, the mesh body at the center of the second disc-shaped mesh 20 is heat-melted at a high temperature and the hot-melted portion mesh body is shaped into the connector 40 by using a mould, so that the degradable filaments constituting the disc-shaped mesh are not easily dispersed and can be firmly connected together. At the same time, the connector 40 and the degradable filaments that make up the disc-shaped mesh can be firmly connected wherein they do not easily fall off.

The connector 40 is tubular and having a height of 1.5-2.0 mm and an outer diameter of 2.5-3.2 mm. The inner mesh surface 11 of the first disc-shaped mesh 10 is concave toward the tubular mesh 30 and the second disc-shaped mesh 20 is concave toward the connector 40. The outer diameter of the first disc-shaped mesh 10 is 5.5-6.5 mm larger than the outer diameter of the second disc-shaped mesh 20. The length of the tubular mesh 30 is 4.5-6.5 mm. The connector 40 is tubular wherein it is provided with an internal thread at an end opposite to the connected mesh surface 20.

The materials of the first disc-shaped mesh 10, the tubular mesh 30, the second disc-shaped mesh 20 and the connector 40 are all macromolecule degradable filaments. The degradable polymer material is one kind of or copolymers of at least two kinds of polylactic acid, polyglycolic acid, polycaprolactone, polydioxanone, polyhydroxybutyrate, polyanhydride, polyphosphate, polyurethane or polycarbonate. The occluder can be filled with polylactic acid film to block the blood flow.

In addition, other parts of this embodiment are the same as the embodiment 1. Therefore it will not be described herein.

Embodiment 3

As shown in FIG. 12, FIG. 13, FIG. 14 and FIG. 15, a degradable cardiac ventricular septal defect occluder includes a first disc-shaped mesh 10, a tubular mesh 30, and a second disc-shaped mesh 20 which are sequentially connected. The first disc-shaped mesh 10 and the second disc-shaped mesh 20 are double-layer mesh covers. The two ends of the tubular mesh 30 are connected to the inner mesh surface 11 of the first disc-shaped mesh 10 and the outer mesh surface 22 of the second disc-shaped mesh 20 respectively. The first disc-shaped mesh 10, the tubular mesh 30, and the second disc-shaped mesh 20 are integrally formed. The center portion of the inner mesh surface 21 of the second disc-shaped mesh 20 is provided with a connector 40 that closes the mesh surface. The inner mesh surface 21 of the second disc-shaped mesh 20 is connected with the connector 40 by hot melt welding. The outer mesh surface 12 of the first disc-shaped mesh 10 includes a closing end 13 wherein the closing end 13 is a plurality of consecutively adjacent ring mesh lines 14. The first disc-shaped mesh 10 is further provided with a closing line 15 wherein the closing line 15 is passed through all the ring mesh lines 14. The outer mesh surface 12 of the first disc-shaped mesh 10 forms a continuous mesh after being closed by the closing line 15. The materials of the first disc-shaped mesh 10, the tubular mesh 30, the second disc-shaped mesh 20 and the connector 40 are all degradable materials.

In the present invention of the occluder, the mesh body at the center of the inner mesh surface of the second disc-shaped mesh 20 is welded by high temperature heat welding as a connector. Specifically, the mesh body at the center of the inner mesh surface of the second disc-shaped mesh 20 is heat-melted at a high temperature and the hot-melted portion mesh body is shaped into the connector 40 by using a mould, so that the degradable filaments constituting the disc-shaped mesh are not easily dispersed and can be firmly connected together. At the same time, the connector 40 and the degradable filaments that make up the disc-shaped mesh can be firmly connected wherein they do not easily fall off.

The connector 40 is tubular, having a height of 1.5-2.0 mm and an outer diameter of 2.5-3.2 mm. The inner mesh surface 21 of the second disc-shaped mesh 20 is concave toward the connector 40. The outer diameter of the first disc-shaped mesh 10 is larger than or equal to the outer diameter of the second disc-shaped mesh 20. The length of the tubular mesh 30 is 3.5-9.5 mm. When the length is 3.5-5.5 mm, it corresponds to the thickness of the defect tissue in the membranous part of ventricle septum; when the length is 6.0-9.5 mm, it corresponds to the thickness of the defect tissue in the muscle part of ventricular septal. The connector 40 is tubular wherein it is provided with an internal thread at an end opposite to the connected mesh surface 21.

The materials of the first disc-shaped mesh 10, the tubular mesh 30, the second disc-shaped mesh 20 and the connector 40 are all macromolecule degradable filaments. The degradable polymer material is one kind of or copolymers of at least two kinds of polylactic acid, polyglycolic acid, polycaprolactone, polydioxanone, polyhydroxybutyrate, polyanhydride, polyphosphate, polyurethane or polycarbonate. The occluder can be filled with polylactic acid film to block the blood flow.

In addition, other parts of this embodiment are the same as the embodiment 1. Therefore it will not be described herein.

Embodiment 4

As shown in FIG. 16, FIG. 17, FIG. 18, FIG. 19 and FIG. 20, a degradable cardiac patent foramen ovale occluder includes a first disc-shaped mesh 10, a tubular mesh 30, and a second disc-shaped mesh 20 which are sequentially connected. The first disc-shaped mesh 10 and the second disc-shaped mesh 20 are double-layer mesh covers. The two ends of the tubular mesh 30 are connected to the inner mesh surface 11 of the first disc-shaped mesh 10 and the inner mesh surface 22 of the second disc-shaped mesh 20 respectively. The first disc-shaped mesh 10, the tubular mesh 30, and the second disc-shaped mesh 20 are integrally formed. The center portion of the outer mesh surface 21 of the second disc-shaped mesh 20 is provided with a connector 40 that closes the mesh surface. The outer mesh surface 21 of the second disc-shaped mesh 20 is connected with the connector 40 by hot melt welding. The outer mesh surface 12 of the first disc-shaped mesh 10 includes a closing end 13 wherein the closing end 13 is a plurality of consecutively adjacent ring mesh lines 14. The first disc-shaped mesh 10 is further provided with a closing line 15 wherein the closing line 15 is passed through all the ring mesh lines 14. The outer mesh surface 12 of the first disc-shaped mesh 10 forms a continuous mesh after being closed by the closing line 15. The materials of the first disc-shaped mesh 10, the tubular mesh 30, the second disc-shaped mesh 20 and the connector 40 are all degradable materials.

In the present invention of the occluder, the mesh body at the center of the outer mesh surface of the second disc-shaped mesh 20 is welded by high temperature heat welding as a connector. Specifically, the mesh body at the center of the outer mesh surface of the second disc-shaped mesh 20 is heat-melted at a high temperature and the hot-melted portion mesh body is shaped into the connector 40 by using a mould, so that the degradable filaments constituting the disc-shaped mesh are not easily dispersed and can be firmly connected together. At the same time, the connector 40 and the degradable filaments that make up the disc-shaped mesh can be firmly connected wherein they do not easily fall off.

The connector 40 is tubular, having a height of 1.5-2.0 mm and an outer diameter of 2.5-3.2 mm. The outer mesh surface 21 of the second disc-shaped mesh 20 is convex toward the connector 40. The outer diameter of the second disc-shaped mesh 10 is larger than or equal to the outer diameter of the first disc-shaped mesh 20. The connector 40 is tubular wherein it is provided with an internal thread at an end opposite to the connected mesh surface 21.

The materials of the first disc-shaped mesh 10, the tubular mesh 30, the second disc-shaped mesh 20 and the connector 40 are all macromolecule degradable filaments. The degradable polymer material is one kind of or copolymers of at least two kinds of polylactic acid, polyglycolic acid, polycaprolactone, polydioxanone, polyhydroxybutyrate, polyanhydride, polyphosphate, polyurethane or polycarbonate. The occluder can be filled with polylactic acid film to block the blood flow.

In addition, other parts of this embodiment are the same as the embodiment 1. Therefore it will not be described herein.

Embodiment 5

As shown in FIG. 21, FIG. 22, FIG. 23, and FIG. 24, a degradable heart left atrial appendage occluder includes a first disc-shaped mesh 10, a tubular mesh 30, and a second disc-shaped mesh 20 which are sequentially connected. The first disc-shaped mesh 10 is a single-layer mesh cover and the second disc-shaped mesh 20 is a double-layer mesh cover. The two ends of the tubular mesh 30 are respectively connected to the first disc mesh 10 and the outer mesh surface 22 of the second disc-shaped mesh 20. The first disc-shaped mesh 10, the tubular mesh 30 and the second disc-shaped mesh 20 are integrally formed. The center of the inner mesh surface 21 of the second disc-shaped mesh 20 is provided with a connector 40 that closes the mesh surface. The inner mesh surface 21 of the second disc-shaped mesh 20 is connected with the connector 40 by hot melt welding. The first disc-shaped mesh 10 includes a closing end 13 wherein the closing end 13 is a plurality of consecutively adjacent ring mesh lines 14. The first disc-shaped mesh is further provided with a closing line 15 wherein the closing line 15 is passed through all the ring mesh lines 14. The first disc-shaped mesh 10 forms a continuous mesh surface after being closed by the closing line 15. The materials of the first disc-shaped mesh 10, the tubular mesh 30, the second disc-shaped mesh 20 and the connector 40 are all degradable materials.

In the present invention of the occluder, the mesh body at the center of the inner mesh surface of the second disc-shaped mesh 20 is welded by high temperature heat welding as a connector. Specifically, the mesh body at the center of the inner mesh surface of the second disc-shaped mesh 20 is heat-melted at a high temperature and the hot-melted portion mesh body is shaped into the connector 40 by using a mould, so that the degradable filaments constituting the disc-shaped mesh are not easily dispersed and can be firmly connected together. At the same time, the connector 40 and the degradable filaments that make up the disc-shaped mesh can be firmly connected wherein they do not easily fall off.

The connector 40 is tubular, having a height of 1.5-2.0 mm and an outer diameter of 2.5-3.2 mm. The inner mesh surface 21 of the second disc-shaped mesh 20 is concave toward the connector 40. The outer diameter of the second disc-shaped mesh 20 is larger than the outer diameter of the first disc-shaped mesh 10. The connector 40 is tubular wherein the connector r 40 is provided with an internal thread at an end opposite to the connected mesh surface 21.

The materials of the first disc-shaped mesh 10, the tubular mesh 30, the second disc-shaped mesh 20 and the connector 40 are all macromolecule degradable filaments. The degradable polymer material is one kind of or copolymers of at least two kinds of polylactic acid, polyglycolic acid, polycaprolactone, polydioxanone, polyhydroxybutyrate, polyanhydride, polyphosphate, polyurethane or polycarbonate. The occluder can be filled with polylactic acid film to block the blood flow.

In addition, other parts of this embodiment are the same as the embodiment 1. Therefore it will not be described herein.

Although specific embodiments of the present invention have been described above, the technicians in the field should understand that these are merely illustrative examples and various changes or modifications can be made to these embodiments without departing from the principle and essence of the present invention. Accordingly, the scope of the invention is defined by the appended claims.

What is claimed is:

1. A degradable occluder, characterized in that the degradable occluder comprises a first disc-shaped mesh, a tubular mesh and a second disc-shaped mesh, which are sequentially connected, wherein two ends of the tubular mesh are respectively connected to the first disc-shaped mesh and the second disc-shaped mesh, wherein the first disc-shaped mesh, the tubular mesh and the second disc-shaped mesh are integrally formed; the second disc-shaped mesh is provided with a connector for closing a mesh surface, wherein the connector is formed by heat-melting a mesh body of the second disc-shaped mesh, wherein materials of the first disc-shaped mesh, the tubular mesh, the second disc-shaped mesh and the connector are all degradable materials; the first disc-shaped mesh comprises a closing end, wherein the closing end is plurality of sequentially adjoining ring mesh lines, wherein the first disc-shaped mesh is further provided with a closing line, wherein the closing line is passed through the plurality of sequentially adjoining ring mesh lines, wherein an outer mesh surface of the first disc-shaped mesh forms a continuous flat mesh surface extending to the closing line after being closed by the closing line, the continuous flat mesh surface is continuous at the closing line;

the connector is tubular without a metal inner tube, and the degradable occluder has no other metal components.

2. The degradable occluder according to claim 1, wherein the degradable occluder is a degradable cardiac atrial septal defect occluder, wherein the first disc-shaped mesh and the second disc-shaped mesh are double-layer mesh covers, wherein two ends of the tubular mesh are respectively connected to an inner mesh surface of the first disc-shaped mesh and an outer mesh surface of the second disc-shaped mesh; the connector is provided at a center of an inner mesh surface of the second disc-shaped mesh, wherein the connector is formed by heat-melting the mesh body at the center of the inner mesh surface of the second disc-shaped mesh.

3. The degradable occluder according to claim 2, wherein the inner mesh surface of the first disc-shaped mesh is concave toward the tubular mesh and the inner mesh surface of the second disc-shaped mesh is concave toward the connector; an outer diameter of the first disc-shaped mesh is 4-6 mm larger than an outer diameter of the second disc-shaped mesh; the outer diameter of the first disc-shaped mesh is 10-16 mm larger than an outer diameter of the tubular mesh; and the tubular mesh has a length of 3.5-5.5 mm.

4. The degradable occluder according to claim 1, wherein the degradable occluder is a degradable cardiac patent ductus arteriosus occluder, wherein the first disc-shaped mesh is a double-layer mesh cover and the second disc-shaped mesh is a single-layer mesh cover, wherein two ends of the tubular mesh are respectively connected to an inner mesh surface of the first disc-shaped mesh and the second disc-shaped mesh; the connector is provided at a center of the second disc-shaped mesh, wherein the connector is formed by heat-melting the mesh body at the center of the second disc-shaped mesh.

5. The degradable occluder of claim 4, wherein the second disc-shaped mesh is concave toward the connector; an outer diameter of the first disc-shaped mesh is 5.5-6.5 mm larger than an outer diameter of the second disc-shaped mesh; and the tubular mesh has a length of 4.5-6.5 mm.

6. The degradable occluder of claim 1, wherein the degradable occluder is a degradable cardiac ventricular septal defect occluder, wherein the first disc-shaped mesh and the second disc-shaped mesh are double-layer mesh covers, wherein two ends of the tubular mesh are respectively connected to an inner mesh surface of the first disc mesh and an outer mesh surface of the second disc mesh; the connector is provided at a center of an inner mesh surface of the second disc-shaped mesh, wherein the connector is formed by heat-melting the mesh body at the center of the inner mesh surface of the second disc-shaped mesh, wherein a height of the tubular mesh is 3.5-9.5 mm.

7. The degradable occluder according to claim 6, wherein the inner mesh surface of the second disc-shaped mesh is concave toward the connector; and an outer diameter of the first disc-shaped mesh is larger than or equal to an outer diameter of the second disc-shaped mesh.

8. The degradable occluder according to claim 6, wherein the tubular mesh has a length of 3.5-5.5 mm.

9. The degradable occluder according to claim 6, wherein the tubular mesh has a length of 6.0-9.5 mm.

10. The degradable occluder according to claim 1, wherein the degradable occluder is a degradable cardiac patent foramen ovale occluder, wherein the first disc-shaped mesh and the second disc-shaped mesh are double-layer mesh covers, wherein two ends of the tubular mesh are respectively connected to an inner mesh surface of the first disc-shaped mesh and an inner mesh surface of the second disc-shaped mesh; wherein the connector is provided at a center of an outer mesh surface of the second disc-shaped mesh, wherein the connector is formed by heat-melting the mesh body at the center of the outer mesh surface of the second disc-shaped mesh, wherein the outer mesh surface of the second disc-shaped mesh is convex toward the connector.

11. The degradable occluder according to claim 10, wherein an outer diameter of the second disc-shaped mesh is larger than or equal to an outer diameter of the first disc-shaped mesh.

12. The degradable occluder according to claim 1, wherein the degradable occluder is a degradable heart left atrial appendage occluder, wherein the first disc-shaped mesh is a single layer mesh cover and the second disc-shaped mesh is a double-layer mesh cover, wherein two ends of the tubular mesh are respectively connected to the first disc-shaped mesh and an outer mesh surface of the second disc-shaped mesh; wherein the connector is provided at a center of an inner mesh surface of the second disc-shaped mesh, wherein the connector is formed by heat-melting the mesh body at the center of the inner mesh surface of the second disc-shaped mesh.

13. The degradable occluder according to claim 12, wherein the inner mesh surface of the second disc-shaped mesh is concave toward the connector; and an outer diameter of the second disc-shaped mesh is larger than an outer diameter of the first disc-shaped mesh.

14. The degradable occluder according to claim 1, wherein a height of the connector is 1.5-2.0 mm; and the connector has an outer diameter of 2.5-3.2 mm.

15. The degradable occluder according to claim 1, wherein all materials of the first disc-shaped mesh, the tubular mesh, the second disc-shaped mesh and the connector are macromolecule degradable filaments.

16. The degradable occluder according to claim 1, wherein the connector is tubular and the connector is provided with internal thread at an end opposite to a connected mesh surface.

17. A mesh tube weaving method for the degradable occluder according to claim 1, characterized in that it comprises inserting a pin into a pin hole of a mould bar, and threading a degradable filament into a needle hole of a sewing needle, and knotting and tightly connecting; tightly knotting a starting point with degradable filaments, and aligning an intersection point between an up line and a down line with a central mark point when weaving to regulate direction of the filament; heat-forming woven mesh tube with the mould bar; and removing the pin and getting the mesh tube after forming.

18. A connector manufacturing method for the degradable occluder according to claim 1, wherein manufacturing steps comprise:
    step 1, closing one end of a mesh tube;
    step 2, placing the mesh tube into a mould;
    step 3, trimming a mesh body;
    step 4, heating a degradable filament;
    step 5, forming an outer shape and an internal thread of the connector;
    step 6, removing the mesh body.

19. The connector manufacturing method according to claim 18, wherein in step 1, lengths of edges of the closing end of the mesh tube are adjusted so that the edges are aligned, and the one end is closed by the degradable filament; in step 2, a closed mesh tube is passed through a sleeve in the mould; in step 3, a part of an original assembly length is used to make the connector, and an excess length of the mesh tube is removed; in step 4, a temperature control device is opened to adjust temperature, and the degradable filament at the connector is continuously heated by heat above the mould, wherein the temperature is adjusted to be 40° C.-100° C. higher than a polymer melting point for heating 5-15 seconds; in step 5, degradable filaments of the connector part are fused together after continuous heating, the temperature control device is removed, and then a slider in the mould is closed, and inserting a thread head of the mould into a slot above the mould for a period of time; and in step 6, after cooling, the thread head of the mould is rotated out of the mould, and the slider is slowly removed, and the mesh body is removed from the mould.

20. A mesh body forming method for the degradable occluder according to claim 1, characterized in that it comprises loading a mesh body with a connector into a mesh body forming mould, and using a jig to fix it and heat-forming it together, and after forming, removing the mesh body from the mould; and filling a degradable membrane into the mesh body with a suture, and closing a closing end to form a flat disc surface.

\* \* \* \* \*